United States Patent
List et al.

(10) Patent No.: US 12,077,608 B2
(45) Date of Patent: Sep. 3, 2024

(54) STAPLED H2 PYRIN PEPTIDES

(71) Applicant: H. LEE MOFFITT CANCER CENTER AND RESEARCH INSTITUTE, INC., Tampa, FL (US)

(72) Inventors: Alan List, Tampa, FL (US); Haitao Ji, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 17/268,818

(22) PCT Filed: Aug. 15, 2019

(86) PCT No.: PCT/US2019/046647
§ 371 (c)(1),
(2) Date: Feb. 16, 2021

(87) PCT Pub. No.: WO2020/037119
PCT Pub. Date: Feb. 20, 2020

(65) Prior Publication Data
US 2021/0238228 A1 Aug. 5, 2021

Related U.S. Application Data

(60) Provisional application No. 62/764,825, filed on Aug. 16, 2018.

(51) Int. Cl.
*C07K 7/08* (2006.01)
*A61K 38/00* (2006.01)

(52) U.S. Cl.
CPC .............. *C07K 7/08* (2013.01); *A61K 38/00* (2013.01)

(58) Field of Classification Search
CPC .......... C07K 7/08; C07K 14/47; A61K 38/00; A61P 35/02; A61P 29/00
See application file for complete search history.

(56) References Cited

U.S. PATENT DOCUMENTS

2016/0354437 A1* 12/2016 Stehlik ............... A61K 38/1709
2018/0050011 A1 2/2018 Wei et al.

FOREIGN PATENT DOCUMENTS

WO WO-2012142604 A2 * 10/2012 ......... A61K 38/1709
WO 2017062518 A1 4/2017
(Continued)

OTHER PUBLICATIONS

Oroz, Journal of Biological Chemistry; 291(37): 19487-19501 (Year: 2016).*

(Continued)

*Primary Examiner* — Kevin S Orwig
*Assistant Examiner* — John Michael Cronin
(74) *Attorney, Agent, or Firm* — Meunier Carlin & Curfman LLC

(57) ABSTRACT

Peptides useful as inflammasome inhibitors are disclosed and can comprise an H2 helix of a pyrin domain, wherein at least two non-consecutive amino acids of the H2 helix are covalently linked. Methods of treating a subject with a disease comprising administering to the subject the disclosed peptides are also disclosed. Further, disclosed herein are methods of inhibiting binding between a first polypeptide comprising a pyrin domain and a second polypeptide comprising a pyrin domain, the method comprising contacting either the first polypeptide or the second polypeptide with the disclosed peptides.

2 Claims, 9 Drawing Sheets

Specification includes a Sequence Listing.

(56) References Cited

FOREIGN PATENT DOCUMENTS

WO         2017136652 A1     8/2017
WO    WO-2017136652 A1 *   8/2017   ........... A61K 38/177

OTHER PUBLICATIONS

Vajjhala et al., Multiple Binding Sites on the Pyrin Domain of ASC Protein Allow Self-association and Interaction with NLRP3 Protein, The Journal of Biological Chemistry vol. 287, No. 50, pp. 41732-41743. (Year: 2012).*

Rao T, Ruiz-Gomez G, Hill TA, Hoang HN, Fairlie DP, et al., Truncated and Helix-Constrained Peptides with High Affinity and Specificity for the cFos Coiled-Coil of AP-1. PLoS ONE 8(3): e59415. doi: 10.1371/journal.pone.0059415 (Year: 2013).*

International Search Report and Written Opinion in PCT/US2019/046647. Mailed Jan. 21, 2020. 12 pages.

Oroz et al. "ASC Pyrin Domain Self-associates and Binds NLRP3 Protein using Equivalent Binding Interfaces" Journal of Biological Chemistry, vol. 291, No. 37, p. 19487-19501: Sep. 9, 2016.

Liepinsh et al. "The Death-domain Fold of the ASC PYRIN Domain, Presenting a Basis for PYRIN/PYRIN recognition". J Mol. Biol. Oct. 3, 2003. vol. 332, No. 5, pp. 1155-1163.

Pal et al. "Inhibition of NLRP3 inflammasome activation by cell-permeable stapled peptides" Scientific Reports, Mar. 20, 2019, vol. 9, p. 4913; whole doc.

* cited by examiner

A  ASC_Q9ULZ3    15  LTAEELKKFKLKLLSVPLREG  35 (SEQ ID NO: 41)
   NLRP3_Q96P20  17  LEDVDLKKFKMHLEDYPPQKG  37 (SEQ ID NO: 42)
   POP1_Q8WXC3   15  LTPEELKKFKMKLGTVPLREG  35 (SEQ ID NO: 43)

B  POP1-H2
   H-EELKKFKMKLGTV-NH$_2$
   (SEQ ID NO: 40)

SAH-POP1-1
   H-ES$_5$KKFS$_5$MKLGTV-NH$_2$
   (SEQ ID NO: 32)

SAH-POP1-2
   H-ER$_8$KKFKMKS$_5$GTV-NH$_2$
   (SEQ ID NO: 33)

SAH-POP1-3
   H-ELKKS$_5$KMKS$_5$GTV-NH$_2$
   (SEQ ID NO: 34)

SAH-POP1-4
   H-ES$_5$LKKS$_5$KMKLGTV-NH$_2$
   (SEQ ID NO: 35)

SAH-POP1-5
   H-ES$_5$LKKS$_5$KWKLGTA-NH$_2$
   (SEQ ID NO: 36)

SAH-POP1-6
   H-ES$_5$LKKS$_5$KFKLGTA-NH$_2$
   (SEQ ID NO: 37)

SAH-POP1-7
   H-ES$_5$LKKS$_5$KHKLGTA-NH$_2$
   (SEQ ID NO: 38)

SAH-POP1-8
   H-ES$_5$LKKS$_5$KN$_L$KLGTA-NH$_2$
   (SEQ ID NO: 39)

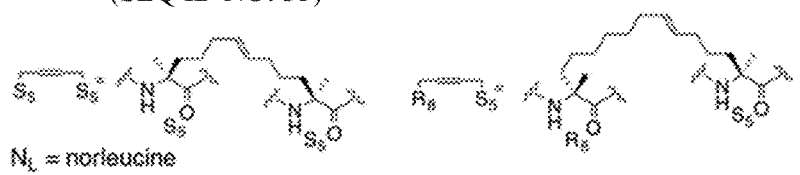

N$_L$ = norleucine

FIG. 1A and FIG. 1B

| No. | Structure | $K_D$ ($\mu M$) NLRP3$^{PYD}$ | ASC$^{PYD}$ | SEQ ID NO |
|---|---|---|---|---|
| fPOP1-H2 | FITC-βA-EELKKFKN$_L$KLGTV-NH$_2$ | 9.2 ± 2.9 | >10 | 2 |
| fSAH-POP1-1 | FITC-βA-ES$_5$KKFS$_5$N$_L$KLGTV-NH$_2$ | 7.1 ± 2.8 | >10 | 1 |
| fSAH-POP1-3 | FITC-βA-ELKKS$_5$KN$_L$KS$_5$GTV-NH$_2$ | >17 | >10 | 3 |
| fSAH-POP1-4 | FITC-βA-ES$_5$LKKS$_5$KN$_L$KLGTV-NH$_2$ | 7.6 ± 2.0 | >10 | 4 |
| fSAH-POP1-5 | FITC-βA-QS$_5$LKKS$_5$KN$_L$KLGTA-NH$_2$ | 11.5 ± 3.5 | >10 | 5 |
| fSAH-POP1-6 | FITC-βA-QS$_5$LKKS$_5$KN$_L$KLWTA-NH$_2$ | 5.9 ± 1.5 | 3.4 ± 0.74 | 6 |
| fSAH-POP1-7 | FITC-βA-QS$_5$LKKS$_5$KN$_L$KLQTA-NH$_2$ | 11.6 ± 4.6 | >10 | 7 |
| fSAH-POP1-8 | FITC-βA-QS$_5$LKKS$_5$KN$_L$KQWTA-NH$_2$ | 9.1 ± 3.0 | >10 | 8 |
| fSAH-POP1-9 | FITC-βA-QS$_5$LKKS$_5$QN$_L$KLWTA-NH$_2$ | 3.8 ± 0.55 | 2.9 ± 0.34 | 9 |
| fSAH-POP1-10 | FITC-βA-QS$_5$LRKS$_5$QN$_L$KLWTA-NH$_2$ | 3.1 ± 0.46 | 1.6 ± 0.18 | 10 |
| fSAH-POP1-11 | FITC-βA-QS$_5$LRKS$_5$QFKLWTA-NH$_2$ | 1.6 ± 0.20 | 1.4 ± 0.16 | 11 |
| fSAH-POP1-12 | FITC-βA-QS$_5$LRKS$_5$QWKLWTA-NH$_2$ | 0.45 ± 0.047 | 0.59 ± 0.061 | 12 |
| fSAH-POP1-13 | FITC-βA-QS$_5$LRRS$_5$QWKLWTA-NH$_2$ | 0.49 ± 0.082 | 0.53 ± 0.085 | 13 |
| fSAH-POP1-14 | FITC-βA-QS$_5$LRRS$_5$QWKLWNA-NH$_2$ | 0.76 ± 0.14 | 0.59 ± 0.092 | 14 |
| fSAH-POP1-15 | FITC-βA-QS$_5$LRRS$_5$QWKLWQA-NH$_2$ | 0.73 ± 0.13 | 0.55 ± 0.092 | 15 |
| fSAH-POP1-16 | FITC-βA-QS$_5$LRRS$_5$QWKLWTS-NH$_2$ | 0.79 ± 0.14 | 0.49 ± 0.091 | 16 |

FIG. 5

| No. | Structure | apparent $K_D$ ($\mu$M) NLRP3$^{PYD}$ | ASC$^{PYD}$ | SEQ ID NO |
|---|---|---|---|---|
| fSAH-POP1-17 | FITC-βA-QS$_5$LRRS$_5$QWB$_1$LWTA-NH$_2$ | 0.068 ± 0.016 | 0.036 ± 0.016 | 17 |
| fSAH-POP1-18 | FITC-βA-QS$_5$LRRS$_5$QWFLWTA-NH$_2$ | 0.069 ± 0.015 | 0.038 ± 0.015 | 18 |
| fSAH-POP1-19 | FITC-βA-QS$_5$LRRS$_5$Q(1-Nal)KLWTA-NH$_2$ | 0.39 ± 0.033 | 0.23 ± 0.065 | 19 |
| fSAH-POP1-20 | FITC-βA-QS$_5$LRRS$_5$Q(2-Nal)KLWTA-NH$_2$ | 0.70 ± 0.093 | 0.27 ± 0.079 | 20 |
| fSAH-POP1-21 | FITC-βA-QS$_5$LRRS$_5$Q(1-Nal)N$_1$LWTA-NH$_2$ | 0.047 ± 0.093 | 0.055 ± 0.025 | 21 |
| fSAH-POP1-22 | FITC-βA-QS$_5$LRRS$_5$Q(2-Nal)N$_1$LWTA-NH$_2$ | 0.044 ± 0.015 | 0.035 ± 0.066 | 22 |

| No. | Structure | $K_D$ (μM) GST-NLRP3$^{PYD}$ | $K_D$ (μM) GST-ASC$^{PYD}$ | SEQ ID NO |
|---|---|---|---|---|
| fPOP1-H2 | FITC-βA-EELKKFKN$_L$KLGTV-NH$_2$ | 27 ± 2.3 | >56 | 2 |
| fSAH-POP1-1 | FITC-βA-ES$_5$KKFS$_5$N$_L$KLGTV-NH$_2$ | 33 ± 2.4 | >56 | 1 |
| fSAH-POP1-3 | FITC-βA-ELKKS$_5$KN$_L$KS$_5$GTV-NH$_2$ | 40 ± 2.6 | >56 | 3 |
| fSAH-POP1-4 | FITC-βA-ES$_5$LKKS$_5$KN$_L$KLGTV-NH$_2$ | 32 ± 2.4 | >56 | 4 |
| fSAH-POP1-5 | FITC-βA-QS$_5$LKKS$_5$KN$_L$KLGTA-NH$_2$ | 30 ± 2.0 | >56 | 5 |
| fSAH-POP1-6 | FITC-βA-QS$_5$LKKS$_5$KN$_L$KLWTA-NH$_2$ | 43 ± 3.3 | >56 | 6 |
| fSAH-POP1-7 | FITC-βA-QS$_5$LKKS$_5$KN$_L$KLWTA-NH$_2$ | 43 ± 4.6 | >56 | 7 |
| fSAH-POP1-8 | FITC-βA-QS$_5$LKKS$_5$KN$_L$KQWTA-NH$_2$ | 55 ± 3.8 | >56 | 8 |
| fSAH-POP1-9 | FITC-βA-QS$_5$LKKS$_5$QN$_L$KLWTA-NH$_2$ | 34 ± 2.1 | >56 | 9 |
| fSAH-POP1-10 | FITC-βA-QS$_5$LKKS$_5$QN$_L$KLWTA-NH$_2$ | 31 ± 2.8 | >56 | 10 |
| fSAH-POP1-11 | FITC-βA-QS$_5$LKKS$_5$QFKLWTA-NH$_2$ | 18 ± 1.7 | >56 | 11 |
| fSAH-POP1-12 | FITC-βA-QS$_5$LKKS$_5$QWKLWTA-NH$_2$ | 20 ± 1.3 | 20 ± 1.9 | 12 |
| fSAH-POP1-13 | FITC-βA-QS$_5$LRRS$_5$QWKLWTA-NH$_2$ | 12 ± 1.9 | 16 ± 2.0 | 13 |
| fSAH-POP1-14 | FITC-βA-QS$_5$LRRS$_5$QWKLWNA-NH$_2$ | 11 ± 0.88 | 14 ± 1.9 | 14 |
| fSAH-POP1-15 | FITC-βA-QS$_5$LRRS$_5$QWKLWQA-NH$_2$ | 13 ± 1.1 | 14 ± 3.3 | 15 |
| fSAH-POP1-16 | FITC-βA-QS$_5$LRRS$_5$QWKLWTS-NH$_2$ | 15 ± 1.4 | 9.2 ± 1.1 | 16 |
| fSAH-POP1-17 | FITC-βA-QS$_5$LRRS$_5$QWN$_L$LWTA-NH$_2$ | 0.38 ± 0.13 | 0.60 ± 0.28 | 17 |
| fSAH-POP1-18 | FITC-βA-QS$_5$LRRS$_5$QWPLWTA-NH$_2$ | 1.6 ± 0.24 | 2.5 ± 0.40 | 18 |
| fSAH-POP1-19 | FITC-βA-QS$_5$LRRS$_5$Q(1-Nal)KLWTA-NH$_2$ | 16 ± 1.6 | >56 | 19 |
| fSAH-POP1-20 | FITC-βA-QS$_5$LRRS$_5$Q(2-Nal)KLWTA-NH$_2$ | 14 ± 1.7 | >56 | 20 |
| fSAH-POP1-21 | FITC-βA-QS$_5$LRRS$_5$Q(1-Nal)N$_L$LWTA-NH$_2$ | 0.25 ± 0.11 | 2.0 ± 0.35 | 21 |
| fSAH-POP1-22 | FITC-βA-QS$_5$LRRS$_5$Q(2-Nal)N$_L$LWTA-NH$_2$ | 0.70 ± 0.16 | 1.4 ± 0.29 | 22 |
| fSAH-POP1-23 | FITC-βA-QS$_5$LRRS$_5$QWN$_L$RWTA-NH$_2$ | 4.3 ± 0.92 | | 23 |
| fSAH-POP1-24 | FITC-βA-QS$_5$SRRS$_5$QWN$_L$RWTA-NH$_2$ | 3.0 ± 0.77 | | 24 |
| fSAH-POP1-25 | FITC-βA-QS$_5$LRRS$_5$QWN$_L$QWTA-NH$_2$ | 5.8 ± 0.57 | 3.0 ± 0.42 | 25 |
| fSAH-POP1-26 | FITC-βA-QS$_5$SRRS$_5$QWN$_L$QWTA-NH$_2$ | 13 ± 1.1 | 5.0 ± 0.79 | 26 |
| fSAH-POP1-27 | FITC-βA-QS$_5$SRRS$_5$KWN$_L$QWTA-NH$_2$ | 7.9 ± 1.1 | 3.9 ± 0.68 | 27 |
| fSAH-POP1-28 | FITC-βA-QS$_5$LRRS$_5$QWN$_L$LGTA-NH$_2$ | 7.7 ± 1.5 | 7.2 ± 1.1 | 28 |
| fSAH-POP1-29 | FITC-βA-QS$_5$LRRS$_5$QWN$_L$LDTA-NH$_2$ | 6.0 ± 0.92 | 5.5 ± 0.69 | 29 |
| fSAH-POP1-30 | FITC-βA-QS$_5$LRRS$_5$QWN$_L$LNTA-NH$_2$ | 6.7 ± 1.2 | 7.5 ± 1.1 | 30 |
| fSAH-POP1-31 | FITC-βA-QS$_5$LRRS$_5$QWN$_L$LSTA-NH$_2$ | 4.7 ± 0.54 | 7.6 ± 1.1 | 31 |

FIG. 10

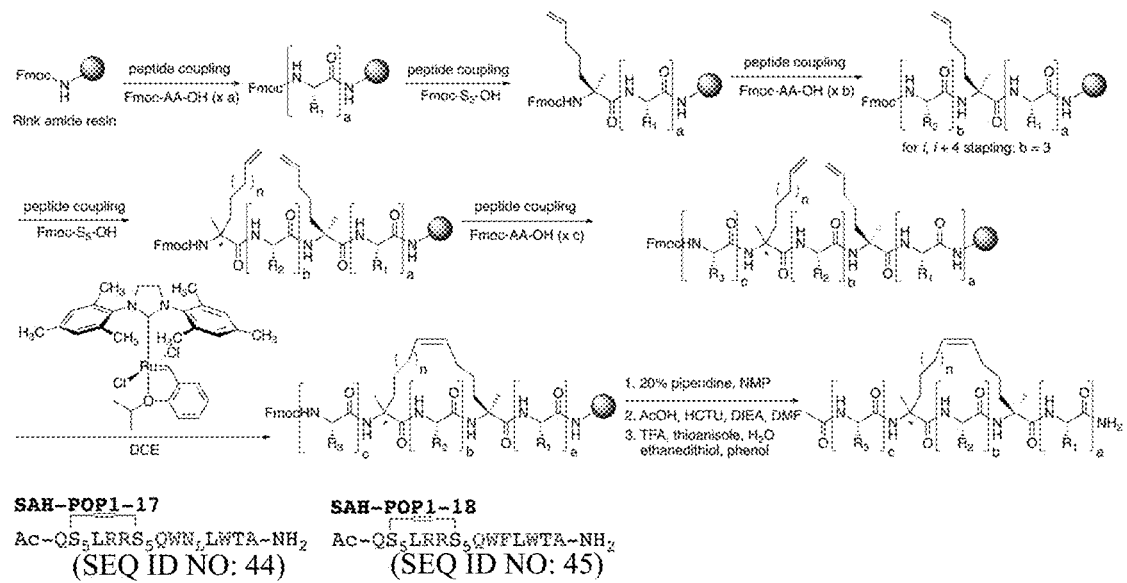
SAH-POP1-17
Ac-QS₅LRRS₅QWN₅LWTA-NH₂
(SEQ ID NO: 44)
SAH-POP1-18
Ac-QS₅LRRS₅QWFLWTA-NH₂
(SEQ ID NO: 45)
FIG. 11
FIG. 12A
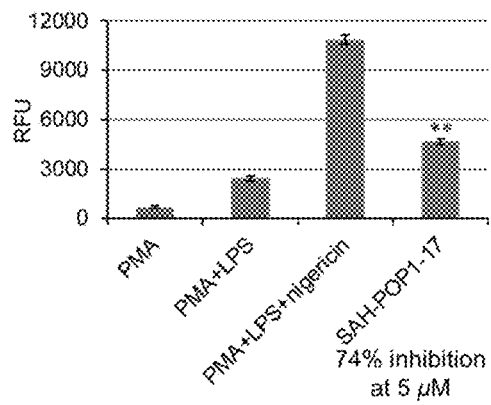
FIG. 12B
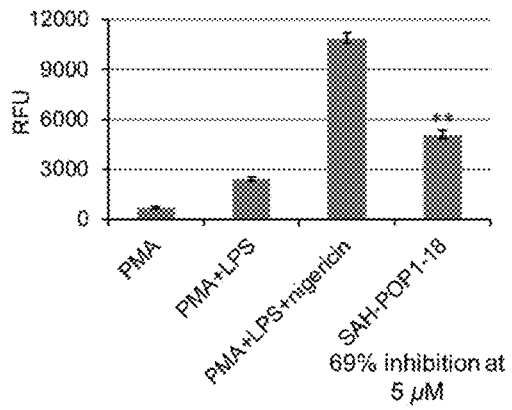
FIG. 12A and FIG. 12B
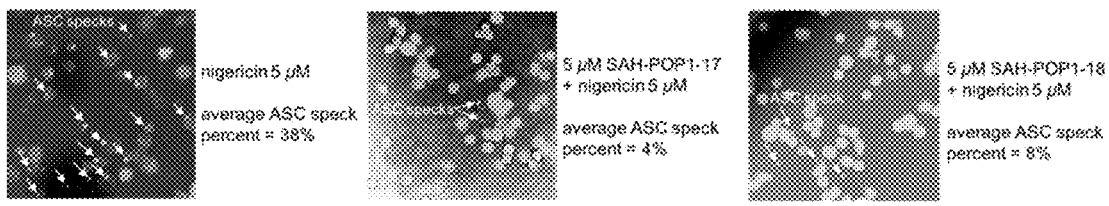
FIG. 13

STAPLED H2 PYRIN PEPTIDES

CROSS REFERENCE TO RELATED APPLICATIONS

This application is a United States National Phase Patent Application of International Patent Application Number PCT/US2019/046647, filed on Aug. 15, 2019, which claims the benefit of priority to U.S. Provisional Application No. 62/764,825, filed Aug. 16, 2018, applications which are incorporated by reference herein in their entirety.

FIELD

The disclosure generally relates to inflammatory diseases and peptides or small molecules used to treat inflammatory diseases.

BACKGROUND

Myelodysplastic syndrome (MDS) is a heterogeneous group of clonal hematopoietic stem cell disorders characterized by bone marrow cytological dysplasia, ineffective hematopoiesis, and a propensity to progress to acute myeloid leukemia (AML). Despite their shared clinical phenotypes, MDSs harbor a diverse array of clonal chromosome abnormalities and somatic gene mutations. Due to the high genetic heterogeneity of the disease and the limited understanding of the molecular abnormalities that contribute to the disease, none of the currently available treatments are curative for MDS.

The inflammation and innate immune system plays an important role in the pathogenesis of MDS. Inflammatory cytokines such as interleukin-1β (IL-1β) and their receptors are significantly up-regulated in MDS. The interaction of the danger-associated molecular pattern (DAMP) heterodimer S100A8/9 with Toll-like receptor 4 (TLR4) and CD33 drives expansion of myeloid-derived suppressor cells (MDSCs) in bone marrow of MDS patients to produce hematopoietic suppressive cytokines. MDS hematopoietic stem and progenitor cells (HSPCs) overexpress key signal molecules of the TLR pathway and activate NF-κB, leading to peripheral blood cytopenias.

The activation of TLRs by DAMPs can trigger pyroptosis, a caspase-1-dependent lytic cell death. Pyroptosis is executed through the formation of inflammasome, a cytosolic, multiprotein complex that is composed of the sensor molecule, such as nucleotide-binding domain (NOD)-like receptor protein 3 (NLRP3), the adaptor protein ASC (apoptosis-associated speck-like protein with a CARD), and the effector protein pro-caspase 1. An inflammasome can activate inflammatory responses and promote maturation and secretion of pro-inflammatory cytokines such as interleukin 1β (IL-1β) and interleukin 18 (IL-18). Inflammasome dysregulation can cause numerous diseases such as autoimmune diseases and auto-inflammatory diseases.

NLRP3 is composed of a central nucleotide-binding and oligomerization domain (NACHT), the N-terminal leucine-rich repeat (LRR), and the C-terminal pyrin domain (PYD). ASC consists of one CARD domain and one PYD domain. Pro-caspase 1 has the CARD and caspase 1 domains. When sensing the external stress signal, the auto-repressed NLRP3 opens up for oligomerization and forms a wheel-shaped signaling hub. The homotypic protein-protein interaction (PPI) between NLRP3 PYD domains (NLRP3$^{PYD}$) forms a disk at the center of this wheel-shaped hub. This NLRP3$^{PYD}$ disk then recruits ASC through the NLRP3$^{PYD}$/ASC$^{PYD}$ PPI. ASC CARD domain recruits the CARD domain of pro-caspase 1, allowing caspase 1 dimerization to form the active caspase 1. Caspase 1 catalyzes the conversion of precursors of the inflammatory cytokines IL-1β and IL-18 to their active forms. Correspondingly, pore formation occurs within the plasma membrane, leading to influx of cations and water, cell swelling, and ultimately osmotic lysis. List and co-workers dissected the role of NLRP3 inflammasome in driving pyroptotic cell death in MDS HSPCs through a series of in vitro and in vivo experiments.

The selective disruption of the NLRP3 inflammasome can offer targeted therapies to eliminate the MDS-initiating clones. Diarylsulfonylureas are known to inhibit caspase 1-dependent IL-1β processing (Perregaux et al., 2001). Among them, glyburide inhibits NLRP3 inflammasome activation (Lamkanfi et al., 2009; Marchetti et al., 2014; Masters et al., 2010). MCC950 (Coll et al., 2015) (also termed CRID3 and CP-456,773 (Coll et al., 2011)), another diarylsulfonylurea-containing compound, also inhibits both canonical and non-canonical activation of the NLRP3 inflammasome. Glutathione S-transferase omega 1-1 was identified as one target for its effects on IL-1β posttranslational processing (Laliberte et al., 2003). MCC950 inhibits NLRP3-induced ASC oligomerization and speck formation in mouse and human macrophages but did not prevent NLRP3 oligomerization or NLRP3/ASC interactions. Later, MCC950 was found to bind with the Walker B motif of the NACHT domain, block ATP hydrolysis, and maintain NLRP3 into the inactive conformation (Coll et al., 2019; Tapia-Abellan et al., 2019). MCC950 attenuated the severity of experimental autoimmune encephalitis, a mouse model of human multiple sclerosis and showed inhibitory effects in mouse models that mirror the human gain-of-function mutations in NLRP3 that lead to the auto-inflammatory Muckle-Wells syndrome (MWS). MCC950 also inhibited IL-1β production of peripheral blood mononuclear cells isolated from patients with MWS. Further structural modifications based on diarylsulfonylurea-containing inhibitors have been reported (Fulp et al., 2018; Hill et al., 2017).

β-Hydroxybutyrate (BHB), a ketone metabolite, inhibits NLRP3-induced ASC oligomerization and speck formation in human macrophages and exhibits in vivo activities using mouse models that have abnormal NLRP3 inflammasome function (Youm et al., 2015). BHB inhibits K$^+$ efflux (Muñoz-Planillo et al., 2013), and its activity is independent of AMP-activated protein kinase, ROS, autophagy, or glycolytic inhibition. Nucleoside reverse transcriptase inhibitors such as zidovudine (AZT) blocks the activity of the ion channel P2X7 and inhibits P2X7-mediated NLRP3 inflammasome activation (Fowler et al., 2014).

25-Hydroxylcholesterol inhibits the function of transcription factor SREBP (sterol response element-binding protein) (Chen et al., 2014) and suppresses expression of the gene that encodes IL-1β (Reboldi et al., 2014).

The stimulation of NLRP3 induces oligomerization of NLRP3$^{PYD}$ (Lu et al., 2014; Sborgi et al., 2015). This oligomer recruits ASC through the NLRP3$^{PYD}$/ASC$^{PYD}$ PPI, resulting in prion nucleation. ASC prion then templates other ASC molecules to form a larger polymer through the ASC$^{PYD}$/ASC$^{PYD}$ PPI. This prion conversion is essential for NLRP3 inflammasome structure and its immune and inflammatory signaling (Cai et al., 2014). PYD only proteins (POPs), including POP1-POP4, are the endogenous negative regulators for the inflammasome (Dorfleutner et al., 2007a; Khare et al., 2014; Porter et al., 2014; Stehlik et al., 2003). They bind with NLRP3 or ASC, inhibit PPIs within and between NLRP3$^{PYD}$ and ASC$^{PYD}$, preventing inflammasome assembly and signaling (Bedoya et al., 2007; de Almeida et al., 2015; Khare et al., 2014). Genetic loss of POPs increases IL-1β levels. Poxvirus that expressed a viral POP can block activation of inflammasomes and NF-κB, and suppress the host immune response (Dorfleutner et al., 2007b; Johnston et al., 2005).

SUMMARY

Disclosed herein are novel peptides which inhibit NLRP3 inflammasome assembly and thus can be used to treat diseases in which inflammasome formation is implicated such as inflammatory diseases. The peptides can contain two or more non-consecutive amino acids which are covalently linked (sometimes referred to herein as "stapled") which stabilizes the peptide in a particular conformation advantageous for inhibiting inflammasome formation. For instance, the peptides can contain at least a portion or all of a helix 2 sequence of a polypeptide pyrin domain, wherein the covalent linkage between the two non-consecutive amino acids stabilizes the sequence in an α-helical structure in solution. Such peptides can be referred to herein as a "stapled pyrin peptide." The disclosed stapled pyrin peptide can inhibit pyrin domain interactions between polypeptides having a pyrin domain, for instance NLRP3 and ASC polypeptides. Thus, for example, a stapled pyrin peptide can inhibit pyrin domain interactions between NLRP3 polypeptides, between ASC polypeptides, and/or between NLRP3 and ASC polypeptides by virtue of interfering with pyrin domain interactions. Further, the disclosed stapled pyrin peptides can inhibit ASC speck formation and/or caspase 1 activation.

In one aspect, disclosed herein are peptides comprising a H2 helix of a pyrin domain, wherein at least two non-consecutive amino acids of the H2 helix are covalently linked (such as, for example, fSAH-POP1-1 (SEQ ID NO: 1), fPOP1-H2 (SEQ ID NO: 2), fSAH-POP1-3 (SEQ ID NO: 3), fSAH-POP1-4 (SEQ ID NO: 4), fSAH-POP1-5 (SEQ ID NO: 5), fSAH-POP1-6 (SEQ ID NO: 6), fSAH-POP1-7 (SEQ ID NO: 7), fSAH-POP1-8 (SEQ ID NO: 8), fSAH-POP1-9 (SEQ ID NO: 9), fSAH-POP1-10 (SEQ ID NO: 10), fSAH-POP1-11 (SEQ ID NO: 11), fSAH-POP1-12 (SEQ ID NO: 12), fSAH-POP1-13 (SEQ ID NO: 13), fSAH-POP1-14 (SEQ ID NO: 14), fSAH-POP1-15 (SEQ ID NO: 15), fSAH-POP1-16 (SEQ ID NO: 16), fSAH-POP1-17 (SEQ ID NO: 17), fSAH-POP1-18 (SEQ ID NO: 18), fSAH-POP1-19 (SEQ ID NO: 19), fSAH-POP1-20 (SEQ ID NO: 20), fSAH-POP1-21 (SEQ ID NO: 21), fSAH-POP1-22 (SEQ ID NO: 22), fSAH-POP1-23 (SEQ ID NO: 23), fSAH-POP1-24 (SEQ ID NO: 24), fSAH-POP1-25 (SEQ ID NO: 25), fSAH-POP1-26 (SEQ ID NO: 26), fSAH-POP1-27 (SEQ ID NO: 27), fSAH-POP1-28 (SEQ ID NO: 28), fSAH-POP1-29 (SEQ ID NO: 29), fSAH-POP1-30 (SEQ ID NO: 30), fSAH-POP1-31 (SEQ ID NO: 31), SAH-POP1-1 (SEQ ID NO: 32), SAH-POP1-2 (SEQ ID NO: 33), SAH-POP1-3 (SEQ ID NO: 34), SAH-POP1-4 (SEQ ID NO: 35), SAH-POP1-5 (SEQ ID NO: 36), SAH-POP1-6 (SEQ ID NO: 37), SAH-POP1-7 (SEQ ID NO: 38), SAH-POP1-8 (SEQ ID NO: 39), SAH-POP1-17 (SEQ ID NO: 44), and SAH-POP1-18 (SEQ ID NO: 45)).

In another aspect, provided herein are methods of treating, preventing, reducing, or inhibiting a disease in a subject (such as, for example, a Myelodysplastic syndrome (MDS) including, but not limited to MDS with multilineage dysplasia (MDS-MLD), MDS with single lineage dysplasia (MDS-SLD), MDS with ring siderolblasts (MDS-RS), MDS with excess blasts, and/or MDS with isolated del(5q) such as, for example, acute myeloid leukemia) comprising administering to the subject a peptide comprising an H2 helix of a pyrin domain, wherein at least two non-consecutive amino acids of the H2 helix are covalently linked (such as, for example, fSAH-POP1-1 (SEQ ID NO: 1), SAH-POP1-3 (SEQ ID NO: 3), fSAH-POP1-4 (SEQ ID NO: 4), fSAH-POP1-5 (SEQ ID NO: 5), fSAH-POP1-6 (SEQ ID NO: 6), fSAH-POP1-7 (SEQ ID NO: 7), fSAH-POP1-8 (SEQ ID NO: 8), fSAH-POP1-9 (SEQ ID NO: 9), fSAH-POP1-10 (SEQ ID NO: 10), fSAH-POP1-11 (SEQ ID NO: 11), fSAH-POP1-12 (SEQ ID NO: 12), fSAH-POP1-13 (SEQ ID NO: 13), fSAH-POP1-14 (SEQ ID NO: 14), fSAH-POP1-15 (SEQ ID NO: 15), fSAH-POP1-16 (SEQ ID NO: 16), fSAH-POP1-17 (SEQ ID NO: 17), fSAH-POP1-18 (SEQ ID NO: 18), fSAH-POP1-19 (SEQ ID NO: 19), fSAH-POP1-20 (SEQ ID NO: 20), fSAH-POP1-21 (SEQ ID NO: 21), fSAH-POP1-22 (SEQ ID NO: 22), fSAH-POP1-23 (SEQ ID NO: 23), fSAH-POP1-24 (SEQ ID NO: 24), fSAH-POP1-25 (SEQ ID NO: 25), fSAH-POP1-26 (SEQ ID NO: 26), fSAH-POP1-27 (SEQ ID NO: 27), fSAH-POP1-28 (SEQ ID NO: 28), fSAH-POP1-29 (SEQ ID NO: 29), fSAH-POP1-30 (SEQ ID NO: 30), fSAH-POP1-31 (SEQ ID NO: 31), SAH-POP1-1 (SEQ ID NO: 32), SAH-POP1-2 (SEQ ID NO: 33), SAH-POP1-3 (SEQ ID NO: 34), SAH-POP1-4 (SEQ ID NO: 35), SAH-POP1-5 (SEQ ID NO: 36), SAH-POP1-6 (SEQ ID NO: 37), SAH-POP1-7 (SEQ ID NO: 38), SAH-POP1-8 (SEQ ID NO: 39), SAH-POP1-17 (SEQ ID NO: 44), and SAH-POP1-18 (SEQ ID NO: 45)).

In another aspect, provided herein are methods of inhibiting binding between a first polypeptide comprising a pyrin domain and a second polypeptide comprising a pyrin domain, the method comprising contacting either the first polypeptide or the second polypeptide with a peptide comprising an H2 helix of a pyrin domain (such as, for example, between NLRP3 polypeptides, between ASC polypeptides, and/or between NLRP3 and ASC polypeptides), wherein at least two non-consecutive amino acids of the H2 helix are covalently linked.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 1A shows sequence alignment of helices H2 of ASC$^{PYD}$ (SEQ ID NO: 41), NLRP3$^{PYD}$ (SEQ ID NO: 42), and POP1$^{PYD}$ (SEQ ID NO: 43). Four key residues for the Ia/Ib PPI interface are shaded. The sequences of α-helices in crystal and NMR structures are underscored. FIG. 1B shows structures of POP1-H2 (SEQ ID NO: 40), SAH-POP1-1 (SEQ ID NO: 32), SAH-POP1-2 (SEQ ID NO: 33), SAH-POP1-3 (SEQ ID NO: 34), SAH-POP1-4 (SEQ ID NO: 35), SAH-POP1-5 (SEQ ID NO: 36), SAH-POP1-6 (SEQ ID NO: 37), SAH-POP1-7 (SEQ ID NO: 38), and SAH-POP1-8

(SEQ ID NO: 39). Lines connecting two amino acids represent a covalent bond between the two indicated amino acids.

Figure 2:
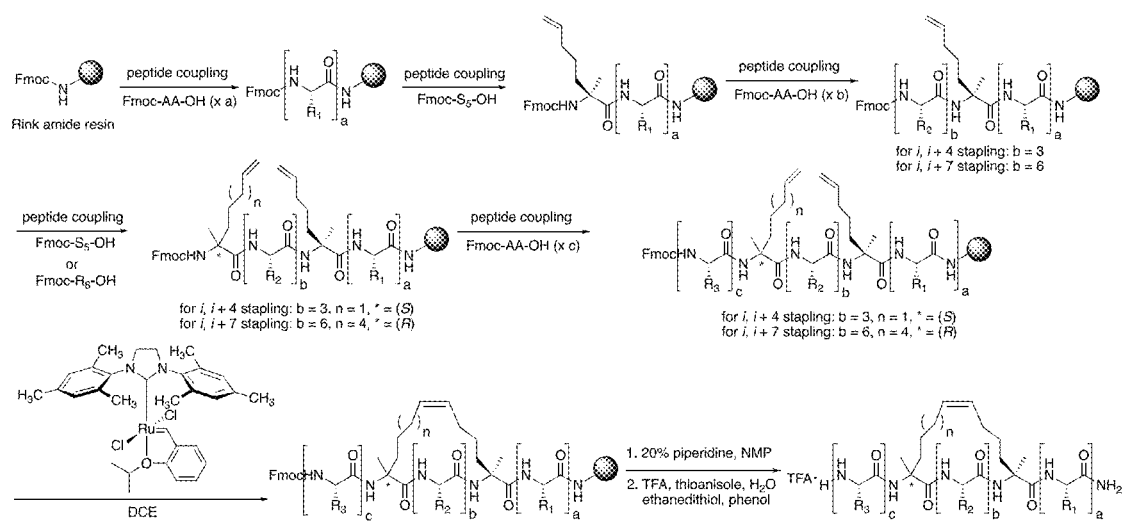

FIG. 2 is a schematic showing the procedure for synthesis of peptides described in FIG. 1B.

Figure 3:
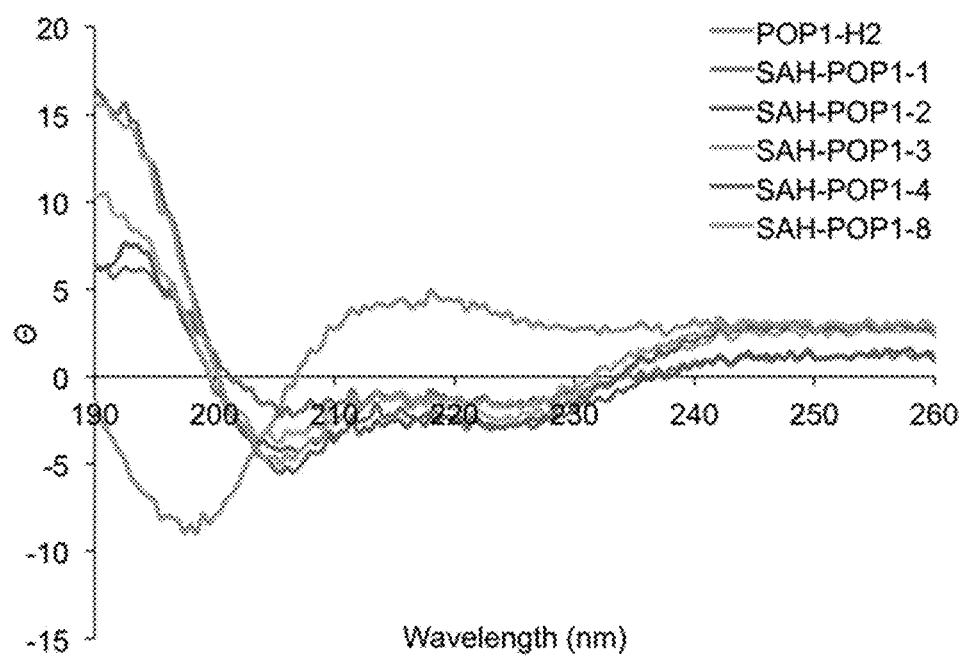

FIG. 3 is a graph showing circular dichroism results of synthesized peptides.

Figure 4:
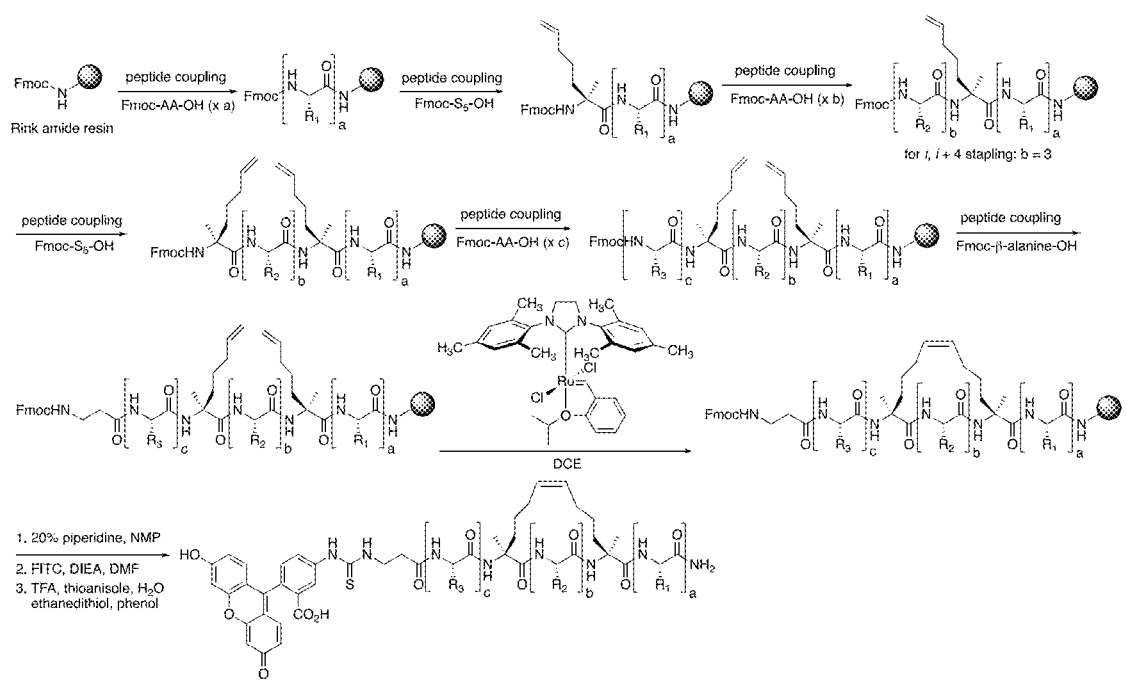

FIG. 4 is a schematic showing the procedure for synthesis of fluorescein (FITC) labeled POP1 stapled peptides.

FIG. 5 is a schematic showing fluorescein polarization (FP) binding assay results for fSAH-POP1-1 (SEQ ID NO: 1), fPOP1-H2 (SEQ ID NO: 2), fSAH-POP1-3 (SEQ ID NO: 3), fSAH-POP1-4 (SEQ ID NO: 4), fSAH-POP1-5 (SEQ ID NO: 5), fSAH-POP1-6 (SEQ ID NO: 6), fSAH-POP1-7 (SEQ ID NO: 7), fSAH-POP1-8 (SEQ ID NO: 8), fSAH-POP1-9 (SEQ ID NO: 9), fSAH-POP1-10 (SEQ ID NO: 10), fSAH-POP1-11 (SEQ ID NO: 11), fSAH-POP1-12 (SEQ ID NO: 12), fSAH-POP1-13 (SEQ ID NO: 13), fSAH-POP1-14 (SEQ ID NO: 14), fSAH-POP1-15 (SEQ ID NO: 15), and fSAH-POP1-16 (SEQ ID NO: 16).

Figures 6A, 6B:
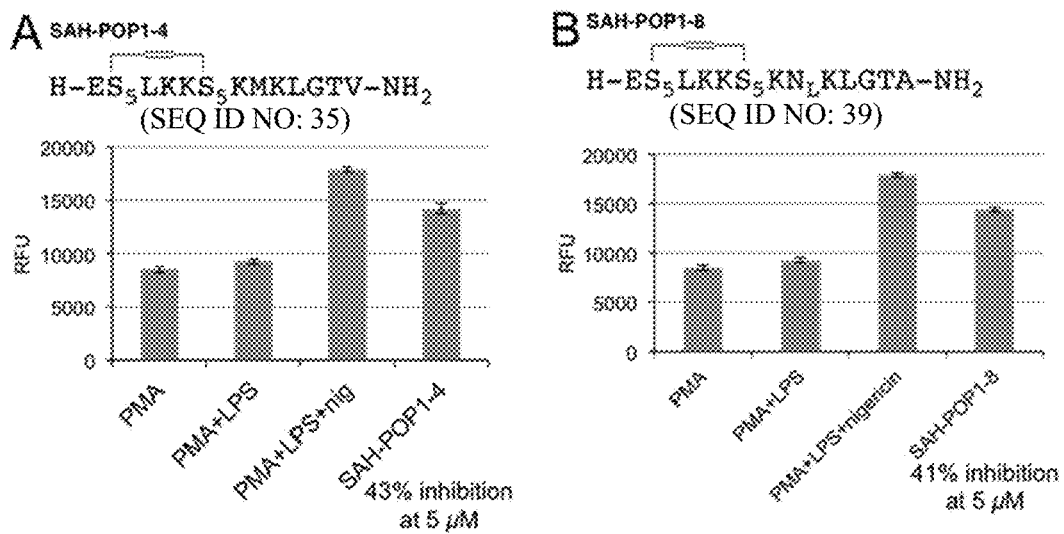

FIG. 6A is a graph showing Promega caspase-Glo™ 1 inflammasome assay results for SAH-POP1-4 (SEQ ID NO: 35). FIG. 6B is a graph showing Promega caspase-Glo™ 1 inflammasome assay results for SAH-POP1-8 (SEQ ID NO: 39).

Figure 7:
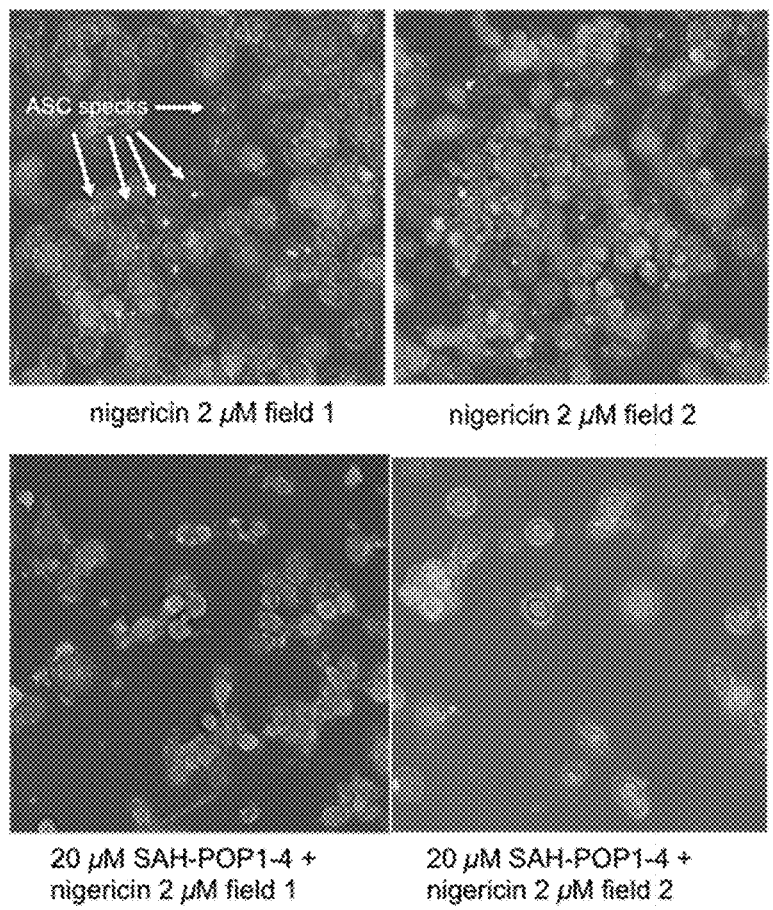

FIG. 7 is a set of images showing live-cell imaging of InvivoGen THP-1 ASC-GFP cells for ASC speck formation. THP-1 ASC-GFP cells with defective NLRP3 were used as the negative control.

Figures 8, 9:
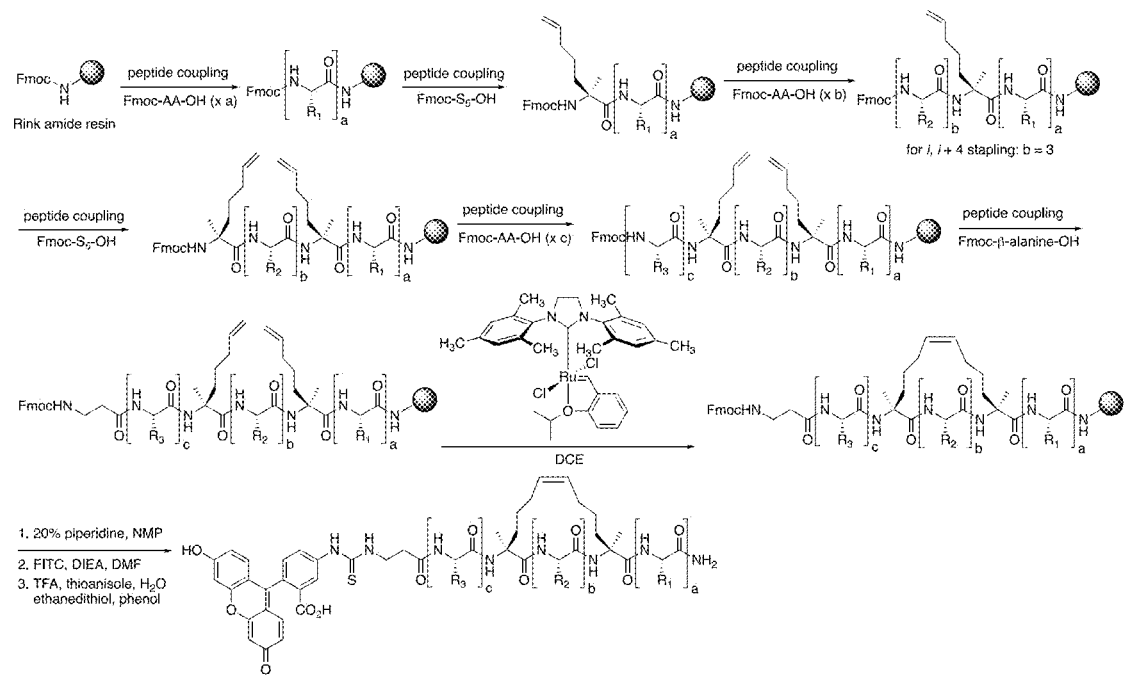

FIG. 8 is a schematic showing the synthesis of fluorescein (FITC) labeled stapled peptides.

FIG. 9. is a table showing results from a FP binding assay to determine the apparent binding affinities of stapled peptides fSAH-POP1-17 (SEQ ID NO: 17), fSAH-POP1-18 (SEQ ID NO: 18), fSAH-POP1-19 (SEQ ID NO: 19), fSAH-POP1-20 (SEQ ID NO: 20), fSAH-POP1-21 (SEQ ID NO: 21), and fSAH-POP1-22 (SEQ ID NO: 22).

FIG. 10 is a table showing the results from a fluorescence anisotropy binding assay to determine the accurate binding affinities of stapled peptides fPOP1-H2 (SEQ ID NO: 2), fSAH-POP1-1 (SEQ ID NO: 1), fSAH-POP1-3 (SEQ ID NO: 3), fSAH-POP1-4 (SEQ ID NO: 4), fSAH-POP1-5 (SEQ ID NO: 5), fSAH-POP1-6 (SEQ ID NO: 6), fSAH-POP1-7 (SEQ ID NO: 7), fSAH-POP1-8 (SEQ ID NO: 8), fSAH-POP1-9 (SEQ ID NO: 9), fSAH-POP1-10 (SEQ ID NO: 10), fSAH-POP1-11 (SEQ ID NO: 11), fSAH-POP1-12 (SEQ ID NO: 12), fSAH-POP1-13 (SEQ ID NO: 13), fSAH-POP1-14 (SEQ ID NO: 14), fSAH-POP1-15 (SEQ ID NO: 15), fSAH-POP1-16 (SEQ ID NO: 16), fSAH-POP1-17 (SEQ ID NO: 17), fSAH-POP1-18 (SEQ ID NO: 18), fSAH-POP1-19 (SEQ ID NO: 19), fSAH-POP1-20 (SEQ ID NO: 20), fSAH-POP1-21 (SEQ ID NO: 21), fSAH-POP1-22 (SEQ ID NO: 22), fSAH-POP1-23 (SEQ ID NO: 23), fSAH-POP1-24 (SEQ ID NO: 24), fSAH-POP1-25 (SEQ ID NO: 25), fSAH-POP1-26 (SEQ ID NO: 26), fSAH-POP1-27 (SEQ ID NO: 27), fSAH-POP1-28 (SEQ ID NO: 28), fSAH-POP1-29 (SEQ ID NO: 29), fSAH-POP1-30 (SEQ ID NO: 30), fSAH-POP1-31 (SEQ ID NO: 31).

FIG. 11 is a schematic showing the synthesis of SAH-POP1-17 (SEQ ID NO: 44) and SAH-POP1-18 (SEQ ID NO: 45).

FIG. 12A is a graph showing Promega caspase-Glo™ 1 inflammasome assay results for SAH-POP1-17.

FIG. 12B is a graph showing Promega caspase-Glo™ 1 inflammasome assay results for SAH-POP1-18.

FIG. 13 shows the inhibition of ASC speck formation by SAH-POP1-17 and SAH-POP1-18. Live-cell imaging of InvivoGen THP-1 ASC-GFP cells was used to visualize ASC speck formation. THP-1 ASC-GFP cells with defective NLRP3 were used as the negative control.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to the peptide are discussed, specifically contemplated is each and every combination and permutation of the peptide and the modifications that are possible unless specifically indicated to the contrary. Thus, if a class of peptides A, B, and C are disclosed as well as a class of peptides D, E, and F and an example of a combination peptide, or, for example, a combination peptide comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

Use of the phrase "and/or" indicates that any one or any combination of a list of options can be used. For example, "A, B, and/or C" means "A", or "B", or "C", or "A and B", or "A and C", or "B and C", or "A and B and C".

As used herein, the terms "can," "may," "optionally," "can optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Grammatical variations of "administer," "administration," and "administering" to a subject include any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

For oral administration, oral compositions such as tablets and capsules may be in unit dose form, and may contain excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl phydroxybenzoate or sorbic acid, and if desired conventional flavoring or coloring agents.

A "control" is an alternative subject, sample, or set of values used in an experiment for comparison purposes. A control can be "positive" or "negative." A control can also be a collection of values used as a standard applied to one or more subjects (e.g., a general number or average that is known and not identified in the method using a sample).

"Identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

"Protein" and "polypeptide" are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

"Peptide" is generally synonymous with protein and polypeptide and is used as such herein. In some embodiments, a peptide can be a fragment of two or more amino acids from a larger polypeptide. In some embodiments, a peptide can be a synthetic molecule essentially identical to a fragment of two or more amino acids from a larger polypeptide. In some embodiments, a peptide can comprise 100 amino acids or less, 90 amino acids or less, 80 amino acids or less, 70 amino acids or less, 60 amino acids or less, 50 amino acids or less, 40 amino acids or less, 30 amino acids or less, 25 amino acids or less, 20 amino acids or less, 15 amino acids or less, or 10 amino acids or less.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

The disclosed compounds may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

"Preventing" a disorder or unwanted physiological event in a subject refers specifically to the prevention of the occurrence of symptoms and/or their underlying cause, wherein the subject may or may not exhibit heightened susceptibility to the disorder or event. As used herein, preventing protein inclusion includes preventing or delaying the initiation of protein inclusion. The term further includes preventing a recurrence of one or more signs or symptoms of protein inclusion.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

The terms "treat," "treating," "treatment," and grammatical variations thereof as used herein, include partially or completely delaying, curing, healing, alleviating, relieving, altering, remedying, ameliorating, improving, stabilizing, mitigating, and/or reducing the intensity or frequency of one or more diseases or conditions, symptoms of a disease or condition, or underlying causes of a disease or condition. Treatments according to the invention may be applied prophylactically, palliatively or remedially. Prophylactic treatments are administered to a subject prior to onset (e.g., before obvious signs of inflammation), during early onset (e.g., upon initial signs and symptoms of inflammation), or after an established development of a disease (e.g., an inflammatory disease). Prophylactic administration can occur for several days to years prior to the manifestation of symptoms.

Compositions

It is understood that the peptides of the present disclosure can be used in combination with the various compositions, methods, products, and applications disclosed herein.

Activated redox-sensitive inflammasomes can drive caspase-1-dependent pyroptotic cell death, inflammatory cytokine generation, and clonal expansion. Inflammasome components can be induced by danger-associated molecular pattern (DAMP) engagement of membrane Toll-like receptors (TLR), whereas cytoplasmic complex assembly is triggered by DAMP interaction with NOD-like receptor proteins (NLRP). Once activated, inflammasomes serve as platforms for caspase-1 activation, IL-1β and IL-18 maturation, cation channel activation and pyroptosis. Neutralization of S100A9 in bone marrow plasma or pharmacologic inhibition of the NLRP3 inflammasome can suppress pyroptosis and reactive oxygen species (ROS).

The disclosure herein addresses needs in the art by providing for polypeptide (e.g., peptide) compositions which can inhibit inflammasome formation. Such peptides are useful at least for treating inflammatory diseases.

Disclosed herein are peptides comprising an H2 helix of a pyrin domain, wherein at least two non-consecutive amino acids of the H2 helix are covalently linked.

In some embodiments, the pyrin domain is from a polypeptide which natively comprises a pyrin domain. In some embodiments, the pyrin domain is from a NLR family pyrin domain containing 3 (NLRP3) polypeptide or a apoptosis-associated speck-like protein containing a CARD (ASC) polypeptide.

In some embodiments, the covalent linkage between the at least two non-consecutive amino acids of the H2 helix stabilizes the H2 helix in an α-helical structure. In some embodiments, the covalent linkage comprises an alkenyl bond. In some embodiments, the covalent linkage is between one or more alanine derivatives.

In some embodiments, the covalent linkage can link any one or more of (S)-2-(4-pentenyl)alanine (referred to herein as "$S_5$"); (S)-2-(7-octenyl)alanine (referred to herein as "$S_8$"); (R)-2-(4-pentenyl)alanine (referred to herein as "$R_5$"); (R)-2-(7-octenyl)alanine (referred to herein as "$R_8$"); bis-pentenylglycine (referred to herein as "$B_5$"); εazido norleucine such as ε-azido-L-norleucine, referred to herein as "ALN", or ε-azido-D-norleucine referred to herein as "ADN"; propargylglycine such as (R)-propargylglycine, referred to herein as "RPPG", or (S)-propargylglycine, referred to herein as "SPPG"; an azidoalanine such as azido-L-alanine, referred to herein as "ALA", or azido-D-alanine, referred to herein as "ADA"; and a dialkynyl linker such as a substituted dialkynyl benzene.

In some embodiments, the covalent linkage is between one or more $S_5$, one or more $S_8$, one or more $R_5$, one or more $R_8$, one or more $B_5$, one or more s-azido norleucine (e.g., one or more ALN; one or more ADN), one or more propargylglycine (e.g., one or more RPPG; one or more SPPG), one or more azidoalanine (e.g., one or more ALA; one or more ADA); or between one or more dialkynyl linker (e.g., one or more substituted dialkynyl benzene). In some embodiments, the covalent linkage is between $S_5$ and $R_5$. In some embodiments, the covalent linkage is between $S_5$ and $R_8$. In some embodiments, the covalent linkage is between $S_5$ and $B_5$. In some embodiments, the covalent linkage is between $S_8$ and $B_5$. In some embodiments, the covalent linkage is between an &-azido norleucine (e.g., ALN, ADN) and a propargylglycine (e.g., RPPG, SPPG). In some embodiments, the covalent linkage is between an azidoalanine (e.g., ALA, ADA) and a dialkynyl linker (e.g., a substituted dialkynyl benzene).

In some embodiments, the at least two non-consecutive amino acids which are covalently linked are separated in the amino acid sequence by at least one, at least two, at least three, at least four, at least five, at least six, at least seven, at least eight, at least nine, or at least ten or more amino acids. In some embodiments, the covalent linkage comprises an alkenyl bond. In some embodiments, the at least two non-consecutive amino acids which are covalently linked are separated in the amino acid sequence by three amino acids. In some embodiments, the at least two non-consecutive amino acids which are covalently linked are separated in the amino acid sequence by six amino acids.

As used herein, a first amino acid which is "non-consecutive" with a second amino acid in the same peptide or polypeptide means that the first amino acid is not directly bonded by a peptide bond with the second amino acid. In other words, in an alphabetical representation of the amino acid sequence, the two non-consecutive numbers are not immediately adjacent to each other in the sequence.

In some embodiments, the peptide comprises an amino acid sequence which is at least 70%, at least 75%, at least 80%, at least 85%, at least 90%, at least 95%, at least 98%, or at least 99% identical to any one or more of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In some embodiments, the peptide comprises any one or more of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Also disclosed herein pharmaceutical compositions comprising a therapeutically effective amount of a pharmaceutically acceptable excipient and a peptide comprising an H2 helix of a pyrin domain, wherein at least two non-consecutive amino acids of the H2 helix are covalently linked. In some embodiments, the polynucleotide is present in a therapeutically effective amount to treat a neurodegenerative disease. Suitable excipients include, but are not limited to, salts, diluents, (e.g., Tris-HCl, acetate, phosphate), preservatives (e.g., Thimerosal, benzyl alcohol, parabens), binders, fillers, solubilizers, disintegrants, sorbents, solvents, pH modifying agents, antioxidants, antinfective agents, suspending agents, wetting agents, viscosity modifiers, tonicity agents, stabilizing agents, and other components and combinations thereof. Suitable pharmaceutically acceptable excipients are preferably selected from materials which are generally recognized as safe (GRAS), and may be administered to an individual without causing undesirable biological side effects or unwanted interactions. Suitable excipients and their formulations are described in Remington's Pharmaceutical Sciences, 16th ed. 1980, Mack Publishing Co. In addition, such compositions can be complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Suitable dosage forms for administration, e.g., parenteral administration, include solutions, suspensions, and emulsions. Typically, the components of the vaccine formulation are dissolved or suspended in a suitable solvent such as, for example, water, Ringer's solution, phosphate buffered saline (PBS), or isotonic sodium chloride. The formulation may also be a sterile solution, suspension, or emulsion in a nontoxic, parenterally acceptable diluent or solvent such as 1,3-butanediol. In some cases, formulations can include one or more tonicity agents to adjust the isotonic range of the formulation. Suitable tonicity agents are well known in the art and include glycerin, mannitol, sorbitol, sodium chloride, and other electrolytes. In some cases, the formulations can be buffered with an effective amount of buffer necessary to maintain a pH suitable for parenteral administration. Suitable buffers are well known by those skilled in the art and some examples of useful buffers are acetate, borate, carbonate, citrate, and phosphate buffers. In some embodiments, the formulation can be distributed or packaged in a liquid form, or alternatively, as a solid, obtained, for example by lyophilization of a suitable liquid formulation, which can be reconstituted with an appropriate carrier or diluent prior to administration. The pharmaceutical compositions comprise a polynucleotide that selectively binds a nucleic acid-binding polypeptide, wherein the nucleic acid-binding polypeptide is capable of intracellular aggregation and is associated with a neurodegenerative disease in a therapeutically effective amount sufficient to treat a neurodegenerative disease. The pharmaceutical compositions can be formulated for medical and/or veterinary use.

In some embodiments, the pharmaceutically acceptable carrier comprises a liposome. In some embodiments of the pharmaceutical composition, the peptide is contained in a liposome or microsphere.

Methods

Also disclosed herein are methods of method of treating a subject with a disease comprising administering to the subject a peptide comprising an H2 helix of a pyrin domain, wherein at least two non-consecutive amino acids of the H2 helix are covalently linked.

Also disclosed are methods of inhibiting binding between a first polypeptide comprising a pyrin domain and a second polypeptide comprising a pyrin domain, the method comprising contacting either the first polypeptide or the second polypeptide with a peptide comprising an H2 helix of a pyrin domain, wherein at least two non-consecutive amino acids of the H2 helix are covalently linked.

The methods can include any herein disclosed peptide comprising an H2 helix of a pyrin domain, wherein at least two non-consecutive amino acids of the H2 helix are covalently linked.

In some embodiments, the methods treat a subject by reducing inflammation and/or pain. In some embodiments, the methods treat a subject by reducing inflammasome formation. In some embodiments, the methods treat a subject by reducing binding between two or more pyrin domains. In some embodiments, the methods treat a subject by reducing ASC speck formation. In some embodiments, the methods treat a subject by reducing caspase 1 activation.

In some embodiments, the disease is an inflammatory disease. In some embodiments, the disease comprises chronic inflammation. Non-limiting examples of inflammatory diseases include arthritis (e.g., osteoarthritis, rheumatoid arthritis, collagen antibody-induced arthritis), asthma, chronic peptic ulcer, tuberculosis, periodontitis, ulcerative colitis, Crohn's disease, sinusitis, hepatitis, bronchitis, appendicitis, dermatitis, meningitis, ankylosing spondylitis, celiac disease, idiopathic pulmonary fibrosis, lupus, systemic lupus erythematosus, psoriasis, type 1 diabetes, Addison's disease, allergy, arthritis, prostatitis, diverticulitis, glomerulonephritis, hidradenitis suppurativa, inflammatory bowel disease, interstitial cystitis, mast cell activation syndrome, mastocytosis, otitis, pelvic inflammatory disease, reperfusion injury, rheumatic fever, rhinitis, sarcoidosis, transplant rejection, vasculitis, atherosclerosis, gout, pleurisy, eczema, gastritis, splenitis, laryngitis, thyroiditis, pharyngitis, multiple sclerosis, myopathies, seborrheic dermatitis, Wegener's granulomatosis, acne vulgaris, Alzheimer's disease, autoimmune diseases, hypersensitivities, Parkinson's disease, etc., and combinations thereof.

In some embodiments, the disease is Myelodysplastic Syndrome (MDS). MDSs are hematological (blood-related) medical conditions with ineffective production (or dysplasia) of the myeloid class of blood cells. In some cases, a subject with MDS has a chromosome 5q deletion (del(5q)). However, in other cases, the subject has non-del5q MDS. In some embodiments, the myeloid disorder is a myelodysplastic/myeloproliferative neoplasms (MDS/MPN). In some cases, the myeloid disorder is a myelodysplastic syndrome with myeloproliferative features. In some cases, the myeloid disorder is a therapy-related myeloid neoplasm.

In some embodiments, the Myelodysplastic Syndrome (MDS) is primary (where no apparent risk factors are found) or secondary (where the MDS develops after being exposed to, for example, chemotherapy or radiation therapy, or exposure to industrial chemicals such as benzene).

The first International Prognostic Scoring System (IPSS) was derived from a study published in 1997 and separates patients into four categories: low risk, intermediate-1 risk, intermediate-2 risk, and high risk (Greenberg P, Cox C, LeBeau M M, et al. International scoring system for evaluating prognosis in myelodysplastic syndromes. Blood 1997; 89:2079-2088). A revised IPSS was developed in 2012 and separates patients into five categories: very low risk, low risk, intermediate risk, high risk, and very high risk (Greenberg P L, Tuechler H, Schanz J, et al. Revised international prognostic scoring system for myelodysplastic syndromes. Blood 2012; 120:2454-2465).

The subject can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers.

The administering step can include at least one, at least two, at least three, at least four, at least five, at least six, at least seven, at least eight, at least nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. In some embodiments, the administering step is performed prior to, concurrent with, or subsequent to the administration of one or more additional diagnostic or therapeutic agents.

In some embodiments, a subsequent administration is provided at least one day after a prior administration, or at least two days, at least three days, at least four days, at least five days, or at least six days after a prior administration. In some embodiments, a subsequent administration is provided at least one week after a prior administration, or at least two weeks, at least three weeks, or at least four weeks after a prior administration. In some embodiments, a subsequent administration is provided at least one month, at least two months, at least three months, at least six months, or at least twelve months after a prior administration.

The amount of the disclosed compositions administered to a subject will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor size). The dosage should not be so large as to outweigh benefits by causing adverse side effects, such as unwanted cross-reactions, anaphylactic reactions, and the like, although some adverse side effects may be expected. The dosage can be adjusted by the individual clinician in the event of any counter indications. Generally, the disclosed compositions and/or formulations are administered to the subject at a dosage of active component(s) ranging from 0.1 μg/kg body weight to 100 g/kg body weight. In some embodiments, the disclosed compositions and/or formulations are administered to the subject at a dosage of active component(s) ranging from 1 μg/kg to 10 g/kg, from 10 μg/kg to 1 g/kg, from 10 μg/kg to 500 mg/kg, from 10 μg/kg to 100 mg/kg, from 10 μg/kg to 10 mg/kg, from 10 μg/kg to 1 mg/kg, from 10 μg/kg to 500 μg/kg, or from 10 μg/kg to 100 μg/kg body weight. Dosages above or below the range cited above may be administered to the individual subject if desired.

A polypeptide comprising a pyrin domain can be any natural or synthetic polypeptide which comprises a pyrin domain. In some embodiments, the polypeptide comprising a pyrin domain is a component of an inflammasome. In some embodiments, the polypeptide comprising a pyrin domain comprises a NLR family pyrin domain containing 3 (NLRP3) polypeptide or an apoptosis-associated speck-like protein containing a CARD (ASC) polypeptide. In some embodiments, a first polypeptide comprising a pyrin domain and a second polypeptide comprising a pyrin domain are different polypeptides. In some embodiments, a first polypeptide comprising a pyrin domain and a second polypeptide comprising a pyrin domain are the same polypeptides. Thus, in some embodiments, the methods can inhibit or reduce polypeptide oligomerization by inhibiting or reducing binding between a first polypeptide comprising a pyrin domain and a second polypeptide comprising a pyrin domain.

In some embodiments, the methods are performed in a cell. In some embodiments, the cell is a myeloid cell. In some embodiments, the cell is a monocyte. In some embodiments, the cell is an inflammatory mediator.

Also disclosed herein are methods of making a peptide comprising an H2 helix of a pyrin domain, wherein at least two non-consecutive amino acids of the H2 helix are covalently linked, the method comprising:
    providing a peptide comprising an H2 helix of a pyrin domain and at least two alanine derivatives selected from (S)-2-(4-pentenyl)alanine ("S$_5$") and Fmoc-(R)-2-(7-octenyl)alanine-OH ("R$_8$"); and
    forming a covalent linkage between the at least two alanine derivatives.

In some embodiments, the covalent linkage is formed by a ring closing reaction. In some embodiments, the method further comprises cleaving a peptidyl resin. In some embodiments, the method further comprises purifying the peptide.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Design and Synthesis of Stapled Peptides

Increased levels of S100 calcium-binding protein A9 (referred to herein as "S100A9"; also known as migration inhibitory factor-related protein 14 (MRP14) or calgranulin B) activated NLRP3 and induced inflammasome assembly. S100A8/9 heterodimers also activated nicotinamide adenine dinucleotide phosphate (NADPH) oxidase, producing reactive oxygen species (ROS) that cause thioredoxin (TRX)-interacting protein (TXNIP) to interact with NLRP3 and activate the inflammasome, driving pyroptosis. Somatic gene mutations also promote ROS generation in MDS (Rassool et al., 2007; Sallmyr et al., 2008), echoing the importance of oxidative stress in MDS (Farquhar and Bowen, 2003). Further, this NLRP3 inflammasome-dependent cell death provides a feed-forward amplification loop, whereby additional DAMPs and ASC are released (Baroja-Mazo et al., 2014; Franklin et al., 2014; Velegraki et al., 2013). ROS also oxidizes and inactivates nucleoredoxin (NRX), dissociates NRX from disheveled (Dvl), and activates Wnt/β-catenin signaling (Kajla et al., 2012; Rharass et al., 2014), enabling the proliferative advantage to the MDS clones.

Based on the crystal and NMR structures of NLRP3$^{PYD}$ (Bae and Park, 2011a; Oroz et al., 2016), NMR structures of ASC PYD domain (ASC$^{PYD}$) (de Alba, 2009; Liepinsh et al., 2003), crystal and NMR structures of POP1 (Choi et al., 2015; Natarajan et al., 2006), and ASC$^{PYD}$ filament structure (Lu et al., 2014; Sborgi et al., 2015), hydrocarbon stapled peptides mimicking helix H2 of pyrin domains were designed and synthesized. These stapled peptides can disrupt the PYD-PYD interaction within NLRP3 and between NLRP3 and ASC, inhibiting inflammasome assembly.

Design and synthesis of the first group of hydrocarbon stapled peptides. Based on the sequence alignment results of helices H2 of ASC$^{PYD}$, NLRP3$^{PYD}$, and POP1$^{PYD}$ in FIG. 1A, nine peptides in FIG. 1B were synthesized. The synthetic route is shown in FIG. 2. After the stapled peptides were synthesized, they were characterized by liquid chromatography-mass spectrometry (LC-MS). The HPLC purities for all peptides were greater than 95%.

Synthetic Procedure (FIG. 2):

Fmoc chemistry for peptide synthesis. Synthesis started from 0.37 mmol/g Rink amide resin, 7.5× excess Fmoc-amino acid (AA)-OH and O-(1H-6-chlorobenzotriazole-1-yl)-1,1,3,3-tetramethyluronium hexafluorophosphate (HCTU), 15× N,N-diisopropylethylamine (DIPEA). The coupling reaction was repeated twice for each position (25 min and 20 min, respectively). The amino acid building blocks used in the reaction are Fmoc-amino acid (AA)-OH, Fmoc-Lys(Boc)-OH for lysine (K), Fmoc-Glu(OtBu)-OH for glutamic acid (E), Fmoc-Thr(tBu)-OH for threonine (T), and S5=(S)-2-(4-pentenyl)alanine or R$_8$=Fmoc-(R)-2-(7-octenyl)alanine-OH, β-alanine at the corresponding positions.

Ring closing reaction. First 1,2-dichloroethane (1,2-DCE) was added to wash resin for 2 times. The resin was then fully protected under nitrogen atmosphere. 0.12 mmol Hoveyda- Grubbs Catalyst™ $2^{nd}$ generation was dissolved in 1 ml of nitrogen-protected 1,2-DCE, and then the catalyst solution was added in 25 μmol peptide resin to react overnight.

Cleavage. After drying, the peptidyl resin was cleaved by the resin cleavage cocktail (90% TFA, 5% thioanisole, 2.5% $H_2O$, 1.5% ethanedithiol, 1% phenol) for 2 h at room temperature Purification. Peptide purification by reversed phase HPLC.

Peptide, Molecular Weight, and Purity:
SAH-POP1-1: [M+H]+=1429.7. HPLC purity >95%
SAH-POP1-2: [M+H]+=1486.8. HPLC purity >95%
SAH-POP1-3: [M+H]+=1409.7. HPLC purity: 95.2%
SAH-POP1-4: [M+H]+=1502.7. HPLC purity: 95.3%
SAH-POP1-5: [M+H]+=1550.9. HPLC purity: 96.6%
SAH-POP1-6: [M+H]+=1512.8. HPLC purity: 95.0%
SAH-POP1-7: [M+H]+=1502.8. HPLC purity: 95.9%
SAH-POP1-8: [M+H]+=1478.8. HPLC purity: 98.4%
Reference peptide POP1-H2: [M+H]+=1550.8. HPLC purity: 99.3%

Example 2: Circular Dichroism (CD) Characteristics of the First Group of Hydrocarbon Stapled Peptides Circular dichroism (CD) was used to determine the secondary structure of the peptides. As shown in FIG. 3, POP1-H2 does not exhibit α-helical structure. Hydrocarbon stapling promoted α-helix contents with SAH-POP1-4 and SAH-POP1-8 having the highest in aqueous solution.

CD spectra were recorded on an AVIV Model 215 Circular Dichroism Spectrometer. Each spectrum was collected with the wavelength between 190 to 260 nm, 0.5 nm increments, and 0.5 s averaging time using a 1-mm path length cell. The peptide concentration was 100 μM in 10 mM potassium phosphate and 100 mM potassium fluoride buffer (pH=7.5). The studied peptides were completely dissolved in this buffer. CD spectra were initially plotted as wavelength versus millidgree, the default output of the instrument. Once the precise peptide concentration was confirmed, the mean residue ellipticity [Θ] was calculated for the y-axis.

Example 3: Overexpression and Purification of Human NLRP3$^{PYD}$

Following the protocols (Bae and Park, 2011a, b; Vajjhala et al., 2012), human NLRP3$^{PYD}$ was overexpressed and purified by Ni-NTA affinity chromatography and size-exclusion chromatography. Briefly, human NLRP3 (residues 3-110) was cloned into a pET-21b vector carrying a C-terminal 6× histidine (Novagen) and transformed into E. coli BL21 DE3 (Novagen). Cells were cultured in LB medium with 50 μg/mL ampicillin until the $OD_{600}$ value was approximately 0.8, and then protein expression was induced with 400 μM IPTG at 20° C. overnight. Cells were lysed by sonication. The proteins were purified by two steps of chromatography, including Ni-NTA affinity chromatography (30210, Qiagen), and size-exclusion chromatography with a HiLoad 26/600 Superdex 200 pg column (28-9893-36, GE Healthcare Life Science) using an AKTA Pure FPLC system (GE Healthcare Life Science). Protein was eluted in a buffer containing 20 mM sodium citrate (pH 5.0) and 2 mM DTT. The purity of human NLRP3$^{PYD}$ was greater than 95% as determined by SDS-PAGE gel analysis. Thermal shift assay was performed on CFX96 Real Time System (Bio-Rad) to monitor protein stability and detect protein aggregation. Protein unfolding was evaluated through measuring the fluorescence changes of fluorescent dye Sypro Orange when interacting with proteins. A temperature increment of 1°/min was applied. All proteins were stable, and no aggregation was observed under storage or assay conditions. Proteins were aliquoted and stored at −80° C.

Example 4: Overexpression and Purification of Human N-Terminally GST Tagged ASC$^{PYD}$ (GST-ASC$^{PYD}$)

N-terminally GST tagged ASC$^{PYD}$ (GST-ASC$^{PYD}$) was purified by glutathione affinity chromatography and size-exclusion chromatography. Briefly, human ASC (residues 1-106) was cloned into a pGEX-4T1 vector carrying an N-terminal GST tag and transformed into E. coli BL21 DE3 (Novagen). Cells were cultured in LB medium with 50 μg/mL ampicillin until the $OD_{600}$ value was approximately 0.8, and then protein expression was induced with 400 μM IPTG at 20° C. overnight. Cells were lysed by sonication. The proteins were purified by two steps of chromatography, including glutathione sepharose 4B (17-0756-01, GE Healthcare Life Science), and size-exclusion chromatography with a HiLoad 26/600 Superdex 200 pg column (28-9893-36, GEHealthcare Life Science) using an AKTA Pure FPLC system (GE Healthcare Life Science). Protein was eluted in a buffer containing 20 mM Tris. HCl (pH 8.0), 100 mM NaCl and 2 mM DTT. The purity of human ASC$^{PYD}$ was greater than 95% as determined by SDS-PAGE gel analysis. Thermal-shift assay was performed on CFX96 Real Time System (Bio-Rad) to monitor protein stability and detect protein aggregation. Protein unfolding was evaluated through measuring the fluorescence changes of fluorescent dye Sypro Orange when interacting with proteins. A temperature increment of 1°/min was applied. All proteins were stable, and no aggregation was observed under storage or assay conditions. Proteins were aliquoted and stored at −80° C.

Example 5: Design and Synthesis of Fluorescein (FITC) Labeled Stapled Peptides

Fluorescein (FITC) labeled POP1 stapled peptides in FIGS. 5 and 9 were synthesized according to the outline described in FIG. 4 and FIG. 8 and characterized (HPLC purities for all peptides >95%).

The synthetic procedure is identical with the previous protocol to produce peptides in FIG. 2, except one step. After the deprotection of Fmoc protecting group after adding the N-terminal amino acid (β-alanine), the resins were incubated with fluorescein isothiocyanate (FITC, 7 equiv.) and DIPEA (14 equiv.) in DMF (0.5 mL) at room temperature for 1 h.

Peptide, Molecular Weight, and Purity:
fSAH-POP1-1: peptide 51 [M+H]+=1872.9. HPLC purity: 95.3%
fSAH-POP1-3: peptide 53 [M+H]+=1854.2. HPLC purity: 98.4%
fSAH-POP1-4: peptide 54 [M+H]+=1966.9. HPLC purity: 95.6%
fSAH-POP1-5: peptide 56 [M+2H]2+=969.2. HPLC purity: 95.7%
fSAH-POP1-6: peptide 57 [M+2H]2+=1034.0. HPLC purity: 95.2%
fSAH-POP1-7: peptide 58 [M+2H]2+=1005.0. HPLC purity: 96.2%
fSAH-POP1-8: peptide 59 [M+2H]2+=1041.2. HPLC purity: 95.9% fSAH-POP1-9: peptide 60 [M+2H]2+=1033.9. HPLC purity: 95.0%
fSAH-POP1-10: peptide 61 [M+2H]2+=1047.8. HPLC purity: 95.1%
fSAH-POP1-11: peptide 62 [M+2H]2+=1065.4. HPLC purity: 95.0%
fSAH-POP1-12: peptide 63 [M+2H]2+=1084.3. HPLC purity: 98.9%
fSAH-POP1-13: peptide 64 [M+2H]2+=1098.2. HPLC purity: >99%
fSAH-POP1-14: peptide 65 [M+2H]2+=1104.8. HPLC purity: >99%
fSAH-POP1-15: peptide 66 [M+2H]2+=1111.9. HPLC purity: >99%
fSAH-POP1-16: peptide 67 [M+2H]2+=1106.3. HPLC purity: 95.1%
fSAH-POP1-17: peptide 68 [M+2H]2+=1090.7. HPLC purity: 98.7%
fSAH-POP1-18: peptide 69 [M+2H]2+=1107.8. HPLC purity: >99%
fSAH-POP1-19: peptide 70 [M+2H]2+=1103.8. HPLC purity: 95.0%
fSAH-POP1-20: peptide 71 [M+2H]2+=1103.8. HPLC purity: 95.2%
fSAH-POP1-21: peptide 72 [M+2H]2+=1096.3. HPLC purity: 95.2%
fSAH-POP1-22: peptide 73 [M+2H]2+=1096.2. HPLC purity: 95.0%
Reference peptide fPOP1-H2: peptide 55 [M+H]+= 1993.0. HPLC purity: 95.0%

As shown in FIG. 3, fPOP1-H2 and fSAH-POP1-4 had similar $K_D$ values with NLRP3$^{PYD}$. The valine (V) residue in fSAH-POP1-4 was changed to alanine (A) in fSAH-POP1-5 to enhance the synthetic accessibility. The glutamate (E) in fSAH-POP1-4 was changed to glutamine (Q) in SAH-POP1-5 to reduce the negative charge and increase the cell permeability. The $K_D$ of fSAH-POP1-5 was 1.5-fold higher than that of fSAH-POP1-4. The glycine (G) of fSAH-POP1-5 was replaced by tryptophan (W) of fSAH-POP1-6 to form the favorable cation-π interaction (Dougherty, 1996, 2013) with NLRP3 R7/ASC R5 based on the know NLRP3$^{PYD}$ and ASC$^{PYD}$ structures and the ASC$^{PYD}$ filament structure. The $K_D$ values of fSAH-POP1-6 is 2-fold lower than fSAH-POP1-5. K24 of ASC$^{PYD}$ (K24 of POP1 and K26 of NLRP3$^{PYD}$) does not form direct interactions with the second ASC$^{PYD}$, and can be replaced by Q in fSAH-POP1-9. K21 of ASC$^{PYD}$ (K21 of POP1 and K23 of NLRP3$^{PYD}$) forms charge-charge interactions with NLRP3 D53/ASC D51. This residue K can be changed to R in fSAH-POP1-10 to increase the cellular penetration (Chu et al., 2015; Lönn and Dowdy, 2015). Norleucine (NL) of fSAH-POP1-10 (M25 of POP1, L25 of ASC$^{PYD}$, M27 of NLRP3$^{PYD}$) was changed to W of fSAH-POP1-12 to enhance the interaction with the hydrophobic pocket formed by NLRP3 R7, L10, A11, A55, 159/ASC R5, 18, L9, T53, V57, as shown in FIG. 7. The binding affinity was dramatically increased 10-fold with the $K_D$ of 0.45 uM. K22 of ASC$^{PYD}$ (K22 of POP1 and K24 of NLRP3$^{PYD}$) forms charge-charge interactions with NLRP3 E15/ASC E13. This residue K can also be changed to R in fSAH-POP1-13 to increase the cell penetrance. When the C-terminal A of fSAH-POP1-13 was changed to a serine (S) residue, fSAH-POP1-16 increased its binding affinity with ASC by forming favorable interactions with ASC R3. The corresponding residue in NLRP3 is S5, which has a side chain that is too far away to form the favorable interaction.

Example 6: Cell-Based Studies

Promega Caspase-Glo™ 1 Inflammasome Assay. A cell-based bioluminescent caspase-1 activity assay (O'Brien et al., 2017) (Promega Caspase-Glo™ I Inflammasome Assay Kit G9951) was used to evaluate the inhibitory activity of SAH-POP1-4 and SAH-POP1-8 on inhibition of inflammasome formation and caspase-1 activation. Human THP-1 monocytes were differentiated with phorbol 12-myristate 13-acetate (PMA), and treated sequentially with lipopolysaccharide (LPS), a Toll-like receptor 4 (TLR4) agonist, and nigericin, a K$^+$ ionophore to promote K$^+$ efflux, resulting in NLRP3- and ASC-dependent caspase-1 activation. The cells were then treated with the inhibitors. As shown in FIG. 6, SAH-POP1-4 and SAH-POP1-8 were cell permeable and inhibited caspase-1 activities (43% and 41%, respectively) at 5 μM.

Experimental Procedure for Promega caspase-Glo™ 1 Inflammasome Assay: THP1 cells were seeded at 5×10$^5$/ml in RPMI1640 medium with 10% FCS in 96-well plates and cultivated in the presence of 50 nM phorbol-12-myristate-13-acetate (PMA) for 24 h. Then the media was replaced with fresh media and incubated for 24 h. The cells were stimulated with 200 ng/ml LPS in E. coli (Sigma) for 3 h. The media was removed and replaced with serum-free media (OptiMEM) containing DMSO (1:1,000), 5 μM inhibitors for 30 min. Cells were then stimulated with the inflammasome activators: 5 μM nigericin 2 h. Control samples were incubated with medium lacking LPS or nigericin. Then the activity of the active caspase-1 was measured by Caspase-Glo™ 1 inflammasome assay (Promega).

Example 7: ASC Speck Assay

ASC speck is a hallmark of inflammasome formation (Dick et al., 2016; Hoss et al., 2017) and observable by microscopy (Doyle et al., 2012; Stutz et al., 2013). THP-1 ASC-GFP cells stably expressing the ASC-GFP fusion protein (InvivoGen Catalog #: thp-ascgfp) were used to visualize the inhibitory effect of SAH-POP1-4 on ASC specks formation (Fernandes-Alnemri et al., 2007). As shown in FIG. 7, nigericin at 2 μM activated ASC speck formation. SAH-POP1-4 at 20 μM completely inhibited ASC speck formation.

Experimental Procedure for ASC Speck Assay. THP1 ASC-GFP cells were seeded at 2×10$^6$/ml (0.7-1 mL) in RPMI1640 medium with 10% FCS in FluoroDish (FD35-100) and cultivated in the presence of 50 nM phorbol-12-myristate-13-acetate (PMA) for 24 h, then media was replaced by fresh media and incubated for 24 h. Then cells were stimulated with 200 ng/ml LPS from E. coli (sigma) for 3 h. The media was removed and replaced with serum-free medium (OptiMEM) containing DMSO (1:1,000), 20 μM inhibitors for 30 min. Cells were then stimulated with the inflammasome activators: 5 μM nigericin for 2 h. Control samples were incubated with media lacking LPS or nigericin. Then, ASC specks were tested by confocal microscopy SP8 (Leica Microsystems).

Example 8: FP Saturation Binding Assay was Used to Determine the Apparent Binding Affinity of the Stapled Peptides The FP experiments were performed in 384-well black plates (262260, Thermo Scientific), and the sample signals were read by a Synergy 2 plate reader (Biotek, Winooski, VT). The polarization was measured at room temperature with an excitation wavelength at 485 nm and an emission wavelength at 535 nm. The FP experiments were performed in an assay buffer of 25 mM HEPES, PH 7.4, 100 mM NaCl, 100 µg/mL of bovine γ-globulin, and 0.01% Triton-X100. The final reaction volume was set to 25 µL. The polarization values were expressed in millipolarization units (mP) and calculated using the following formula $$mP = \frac{1000(I_s - GI_p)}{I_s + GI_p}$$

Where $I_s$ and $I_p$ were the parallel and perpendicular emission intensities of the sample respectively. G, the G factor, was determined to be 0.999.

The FP assays used 12.5 nM stapled peptide fluorescent tracer, 10 µM His6-NLRP3$^{PYD}$ or GST-ASC$^{PYD}$ and different concentrations of the tested inhibitors in 25 µL of assay buffer. Each assay plate was covered black and gently mixed on an orbital shaker for 3 h to reach equilibrium before the polarization values were recorded. The data was analyzed by nonlinear least-square analyses using GraphPad Prism 5.0. Each experiment was performed in triplicate, and the results were expressed as mean±standard deviation. The result is shown in FIG. 9.

Example 9: Fluorescence Anisotropy Binding Assay to Determine the Accurate Binding Affinity of the Stapled Peptides The fluorescence anisotropy binding assays were performed in 384-well Microfluor 2 black plates (262260, Thermo Fisher Scientific), and the sample signals were read by a Synergy 2 plate reader (Biotek). The experiments were performed in an assay buffer of 25 mM HEPES, PH 7.4, 100 mM NaCl, 100 µg/mL of bovine γ-globulin, and 0.01% Triton-X100. The concentration of stapled peptide fluorescent tracer was fixed at 12.5 nM. Different concentrations of GST-NLRP3 were added to the assay buffer giving a final volume of 25 µL. After the addition, each assay plate was covered and gently mixed on an orbital shaker for 2 h before the data were recorded at room temperature with an excitation wavelength at 485 nm and an emission wavelength at 535 nm. Each experiment was repeated for three times, and the results were expressed as mean±standard deviation. The parallel fluorescence intensity ($I_s$), the perpendicular fluorescence intensity ($I_p$), and the anisotropy (r) were recorded directly by the plate reader. The total intensity (I), the fraction ligand bound ($L_b$) was calculated by equations 1 and 2 shown below.

$$I = 2 \times I_p \times G + I_s \quad \text{(eq. 1)}$$

G: the G factor. It was 0.999 for the instrument used $$L_b = \frac{r - r_{min}}{\lambda \times (r_{max} - r) + (r - r_{min})} \quad \text{(eq. 2)}$$

$r_{min}$: the average anisotropy value for the fluorescently labeled POP1 stapled peptide $r_{max}$: the average anisotropy value for the fluorescently labeled POP1 stapled peptide with saturated GST-NLRP3$^{PYD}$ or GST-ASC$^{PYD}$ $$\lambda = \frac{I_{bound}}{I_{unbound}}$$

$I_{bound}$: the average intensity value for the fluorescently labeled POP1 stapled peptide with saturated GST-NLRP3$^{PYD}$ or GST-ASC$^{PYD}$ $I_{unbound}$: the average intensity value for the fluorescently labeled POP1 stapled peptide The above data was then imported to GraphPad Prism 5.0, and the $K_D$ values between GST-NLRP3$^{PYD}$ or GST-ASC$^{PYD}$ and fluorescently labeled stapled peptide were analyzed by the nonlinear regression equation (eq. 3) shown below.

$$Y = \frac{(K_d + X + [\text{fluorescent tracer}]) - \sqrt{(K_D + X + [\text{fluorescent} - \text{tracer}])^2 - 4 \times X \times [\text{fluorescent} - \text{tracer}]}}{2} \quad \text{(eq. 3)}$$

Y=$L_b$×[fluorescent-tracer]. [fluorescent-tracer], the concentration of the fluorecein-labeled stapled peptide was 10 nM.

X=[GST-NLRP3$^{PYD}$] or [GST-ASC$^{PYD}$]

fSAH-POP1-1: peptide 51 [M+H]+=1872.9. HPLC purity: 95.3% fSAH-POP1-3: peptide 53 [M+H]+=1854.2. HPLC purity: 98.4% fSAH-POP1-4: peptide 54 [M+H]+=1966.9. HPLC purity: 95.6% fSAH-POP1-5: peptide 56 [M+2H]2+=969.2. HPLC purity: 95.7% fSAH-POP1-6: peptide 57 [M+2H]2+=1034.0. HPLC purity: 95.2% fSAH-POP1-7: peptide 58 [M+2H]2+=1005.0. HPLC purity: 96.2% fSAH-POP1-8: peptide 59 [M+2H]2+=1041.2. HPLC purity: 95.9% fSAH-POP1-9: peptide 60 [M+2H]2+=1033.9. HPLC purity: 95.0% fSAH-POP1-10: peptide 61 [M+2H]2+=1047.8. HPLC purity: 95.1% fSAH-POP1-11: peptide 62 [M+2H]2+=1065.4. HPLC purity: 95.0% fSAH-POP1-12: peptide 63 [M+2H]2+=1084.3. HPLC purity: 98.9% fSAH-POP1-13: peptide 64 [M+2H]2+=1098.2. HPLC purity: >99% fSAH-POP1-14: peptide 65 [M+2H]2+=1104.8. HPLC purity: >99% fSAH-POP1-15: peptide 66 [M+2H]2+=1111.9. HPLC purity: >99% fSAH-POP1-16: peptide 67 [M+2H]2+=1106.3. HPLC purity: 95.1% fSAH-POP1-17: peptide 68 [M+2H]2+=1090.7. HPLC purity: 98.7% fSAH-POP1-18: peptide 69 [M+2H]2+=1107.8. HPLC purity: 100% fSAH-POP1-19: peptide 70 [M+2H]2+=1103.8. HPLC purity: 95.0%
fSAH-POP1-20: peptide 71 [M+2H]2+=1103.8. HPLC purity: 95.2%
fSAH-POP1-21: peptide 72 [M+2H]2+=1096.3. HPLC purity: 95.2%
fSAH-POP1-22: peptide 73 [M+2H]2+=1096.2. HPLC purity: 95.0%
fSAH-POP1-23: peptide 76 [M+2H]2+=1112.3. HPLC purity: 95.2%
fSAH-POP1-24: peptide 77 [M+2H]2+=1099.2. HPLC purity: 98.6%
fSAH-POP1-25: peptide 78 [M+2H]2+=1098.3. HPLC purity: 97.3%
fSAH-POP1-26: peptide 79 [M+2H]2+=1085.2. HPLC purity: 96.2%
fSAH-POP1-27: peptide 80 [M+2H]2+=1085.2. HPLC purity: 96.4%
fSAH-POP1-28: peptide 81 [M+2H]2+=1026.2. HPLC purity: 95.3%
fSAH-POP1-29: peptide 82 [M+2H]2+=1055.5. HPLC purity: 95.6%
fSAH-POP1-30: peptide 83 [M+2H]2+=1054.8. HPLC purity: 95.4%
fSAH-POP1-31: peptide 84 [M+2H]2+=1041.3. HPLC purity: 95.1%

Example 10: Synthesis of Stapled Peptides SAH-POP1-17 and SAH-POP1-18

Stapled peptides SAH-POP1-17 and SAH-POP1-18 were synthesized by the FIG. 11 and characterized (HPLC purities for all peptides >95%).

Fmoc chemistry for peptide synthesis. Synthesis start from 0.37 mmol/g Rink amide resin, 7.5× excess Fmoc-amino acid (AA)-OH and O-(1H-6-chlorobenzotriazole-1-yl)-1,1,3,3-tetramethyluronium hexafluorophosphate (HCTU), 15× N,N-diisopropylethylamine (DIPEA). The coupling reaction was repeated twice for each position (25 min and 20 min, respectively). The amino acid building blocks used in the reaction are Fmoc-amino acid (AA)-OH, Fmoc-Lys(Boc)-OH for lysine (K), Fmoc-Glu(OtBu)-OH for glutamic acid (E), Fmoc-Thr(tBu)-OH for threonine (T), and S5=(S)-2-(4-pentenyl)alanine, and AcOH at the corresponding positions.

Ring closing reaction. First add 1,2-dichloroethane (1,2-DCE) to wash resin for 2 times. The resin is then fully protected under nitrogen atmosphere. 0.12 mmol Hoveyda-Grubbs Catalyst™ $2^{nd}$ generation was dissolved in 1 ml of nitrogen-protected 1,2-DCE, and then add the catalyst solution in 25 umol peptide resin to react overnight.

Cleavage. After drying, the peptidyl resin was cleaved by the resin cleavage cocktail (90% TFA, 5% thioanisole, 2.5% H$_2$O, 1.5% ethanedithiol, 1% phenol) for 2 h at room temperature Purification. Peptide purification by reversed phase HPLC.

Example 11: Cell-Based Studies of SAH-POP1-17 and SAH-POP1-18

A cell-based bioluminescent caspase-1 activity assay (Promega Caspase-Glo™ 1 Inflammasome Assay Kit G9951) was used to evaluate the inhibitory activity of SAH-POP1-17 and SAH-POP1-18 on inhibition of inflammasome formation and caspase-1 activation. Human THP-1 monocytes were differentiated with phorbol 12-myristate 13-acetate (PMA), and treated sequentially with lipopolysaccharide (LPS), a Toll-like receptor 4 (TLR4) agonist, and nigericin, a K$^+$ ionophore to promote K$^+$ efflux, resulting in NLRP3- and ASC-dependent caspase-1 activation. The cells were then treated with the inhibitors. As shown in FIGS. 6A and 6B, SAH-POP1-4 and SAH-POP1-8 were cell permeable and inhibited caspase-1 activities (43% and 41%, respectively) at 5 μM.

Experimental Procedure for Promega caspase-Glo™ 1 Inflammasome Assay: THP1 cells were seeded at 5×10$^5$/ml in RPMI1640 medium with 10% FCS in 96-well plates and cultivated in the presence of 50 nM phorbol-12-myristate-13-acetate (PMA) for 24 h. Then the media was replaced with fresh media and incubated for 24 h. The cells were stimulated with 200 ng/ml LPS in E. coli (Sigma) for 3 h. The media was removed and replaced with serum-free media (OptiMEM) containing DMSO (1:1,000), 5 μM inhibitors for 30 min. Cells were then stimulated with the inflammasome activators: 5 μM nigericin 2 h. Control samples were incubated with medium lacking LPS or nigericin. Then the activity of the active caspase-1 was measured by Caspase-Glo™ 1 inflammasome assay (Promega).

Example 12: ASC Speck Assay

ASC speck is the hallmark of inflammasome formation and observable by microscopy. THP-1 ASC-GFP cells stably expressing the ASC-GFP fusion protein (InvivoGen Catalog #: thp-ascgfp) were used to visualize the inhibitory effect of SAH-POP1-17 on ASC specks formation (Fernandes-Alnemri et al., 2007). As shown in FIG. 13, nigericin at 5 μM activated ASC speck formation to 38%. SAH-POP1-17 at 5 μM inhibited ASC speck formation to 4%, and SAH-POP1-18 at 5 μM inhibited ASC speck formation to 8%.

Experimental Procedure for ASC Speck Assay. THP1 ASC-GFP cells were seeded at 2×10$^6$/ml (0.7-1 mL) in RPMI1640 medium with 10% FCS in FluoroDish (FD35-100) and cultivated in the presence of 50 nM phorbol-12-myristate-13-acetate (PMA) for 24 h, then media was replaced by fresh media and incubated for 24 h. Then cells were stimulated with 200 ng/ml LPS from E. coli (sigma) for 3 h. The media was removed and replaced with serum-free medium (OptiMEM) containing DMSO (1:1,000), 20 μM inhibitors for 30 min. Cells were then stimulated with the inflammasome activators: 5 μM nigericin for 2 h. Control samples were incubated with media lacking LPS or nigericin. Then, ASC specks were tested by confocal microscopy SP8 (Leica Microsystems).

Sequences.
SEQ ID NO:32. A SAH-POP1-1 amino acid sequence. ES$_5$KKFS$_5$MKLGTV
SEQ ID NO:33. A SAH-POP1-2 amino acid sequence. ER$_8$KKFKMKS$_5$GTV
SEQ ID NO:34. A SAH-POP1-3 amino acid sequence. ELKKS$_5$KMKS$_5$GTV
SEQ ID NO:35. A SAH-POP1-4 amino acid sequence. ES$_5$LKKS$_5$KMKLGTV
SEQ ID NO:36. A SAH-POP1-5 amino acid sequence. ES$_5$LKKS$_5$KWKLGTA
SEQ ID NO:37. A SAH-POP1-6 amino acid sequence. ESLKKSKFKLGTA
SEQ ID NO:38. A SAH-POP1-7 amino acid sequence. ES$_5$LKKS$_5$KHKLGTA
SEQ ID NO:39. A SAH-POP1-8 amino acid sequence. ES$_5$LKKS$_5$KN$_L$KLGTA
SEQ ID NO:40. A POP1-H2 amino acid sequence. EELKKFKMKLGTV SEQ ID NO: 41 ASC$^{PYD}$ amino acid sequence
LTAEELKKFKLKLLSVPLREG In each sequence listing of this Example, the following amino acid analogues can be used: $S_5$=(S)-2-(4-pentenyl) alanine; $R_8$=Fmoc-(R)-2-(7-octenyl)alanine-OH; $N_L$=norleucine. In each sequence listing of this Example, a covalent bond (e.g., an alkenyl bond) can be formed between at least two $S_5$, at least two $R_8$, or between a $S_5$ and a $R_8$.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

REFERENCES

Abais, J. M., Xia, M., Zhang, Y., Boini, K. M., and Li, P. L. (2015). Redox regulation of NLRP3 inflammasomes: ROS as trigger or effector? Antioxid Redox Signal 22, 1111-1129.

Bae, J. Y., and Park, H. H. (2011a). Crystal structure of NALP3 protein pyrin domain (PYD) and its implications in inflammasome assembly. J Biol Chem 286, 39528-39536.

Bae, J. Y., and Park, H. H. (2011b). Crystallization and preliminary X-ray crystallographic studies of the PYD domain of human NALP3. Acta crystallographica Section F, Structural biology and crystallization communications 67, 1421-1424.

Baroja-Mazo, A., Martín-Sánchez, F., Gomez, A. I., Martínez, C. M., Amores-Iniesta, J., Compan, V., Barberà-Cremades, M., Yagüe, J., Ruiz-Ortiz, E., Antón, J., et al. (2014). The NLRP3 inflammasome is released as a particulate danger signal that amplifies the inflammatory response. Nat Immunol 15, 738-748.

Basiorka, A. A., McGraw, K. L., Eksioglu, E. A., Chen, X., Johnson, J., Zhang, L., Zhang, Q., Irvine, B. A., Cluzeau, T., Sallman, D. A., et al. (2016). The NLRP3 inflammasome functions as a driver of the myelodysplastic syndrome phenotype. Blood 128, 2960-2975.

Bedoya, F., Sandler, L. L., and Harton, J. A. (2007). Pyrin-only protein 2 modulates NF-κB and disrupts ASC:CLR interactions. J Immunol 178, 3837-3845.

Bejar, R., Stevenson, K., Abdel-Wahab, O., Galili, N., Nilsson, B., Garcia-Manero, G., Kantarjian, H., Raza, A., Levine, R. L., Neuberg, D., et al. (2011). Clinical effect of point mutations in myelodysplastic syndromes. The New England journal of medicine 364, 2496-2506.

Bergsbaken, T., Fink, S. L., and Cookson, B. T. (2009). Pyroptosis: host cell death and inflammation. Nat Rev Microbiol 7, 99-109.

Bird, G. H., Bernal, F., Pitter, K., and Walensky, L. D. (2008). Synthesis and biophysical characterization of stabilized alpha-helices of BCL-2 domains. Methods in enzymology 446, 369-386.

Boldin, M. P., Taganov, K. D., Rao, D. S., Yang, L., Zhao, J. L., Kalwani, M., Garcia-Flores, Y., Luong, M., Devrekanli, A., Xu, J., et al. (2011). miR-146a is a significant brake on autoimmunity, myeloproliferation, and cancer in mice. J Exp Med 208, 1189-1201.

Braun, T., Carvalho, G., Coquelle, A., Vozenin, M.-C., Lepelley, P., Hirsch, F., Kiladjian, J.-J., Ribrag, V., Fenaux, P., and Kroemer, G. (2006). NF-κB constitutes a potential therapeutic target in high-risk myelodysplastic syndrome. Blood 107, 1156-1165.

Broz, P., and Dixit, V. M. (2016). Inflammasomes: mechanism of assembly, regulation and signalling. Nat Rev Immunol 16, 407-420.

Cai, X., Chen, J., Xu, H., Liu, S., Jiang, Q.-X., Halfmann, R., and Chen, Z. J. (2014). Prion-like polymerization underlies signal transduction in antiviral immune defense and inflammasome activation. Cell 156, 1207-1222.

Chen, X., Eksioglu, E. A., Zhou, J., Zhang, L., Djeu, J., Fortenbery, N., Epling-Burnette, P., Van Bijnen, S., Dolstra, H., Cannon, J., et al. (2013). Induction of myelodysplasia by myeloid-derived suppressor cells. J Clin Invest 123, 4595-4611.

Chen, Z., Martin, M., Li, Z., and Shyy, J. Y.-J. (2014). Endothelial dysfunction: the role of sterol regulatory element-binding protein-induced NOD-like receptor family pyrin domain-containing protein 3 inflammasome in atherosclerosis. Curr Opin Lipidol 25, 339-349.

Choi, J. Y., Kim, C. M., Seo, E. K., Bhat, E. A., Jang, T.-h., Lee, J. H., and Park, H. H. (2015). Crystal structure of human POP1 and its distinct structural feature for PYD domain. Biochem Biophys Res Commun 460, 957-963.

Chu, Q., Moellering, R. E., Hilinski, G. J., Kim, Y.-W., Grossmann, T. N., Yeh, J. T.-H., and Verdine, G. L. (2015). Towards understanding cell penetration by stapled peptides. Med Chem Comm 6, 111-119.

Coll, R. C., Robertson, A., Butler, M., Cooper, M., and O'Neill, L. A. (2011). The cytokine release inhibitory drug CRID3 targets ASC oligomerisation in the NLRP3 and AIM2 inflammasomes. PLOS One 6, e29539.

Coll, R. C., Robertson, A. A. B., Chae, J. J., Higgins, S. C., Muñoz-Planillo, R., Inserra, M. C., Vetter, I., Dungan, L. S., Monks, B. G., Stutz, A., et al. (2015). A small-molecule inhibitor of the NLRP3 inflammasome for the treatment of inflammatory diseases. Nat Med 21, 248-255.

Daniels, M. J. D., Rivers-Auty, J., Schilling, T., Spencer, N. G., Watremez, W., Fasolino, V., Booth, S. J., White, C. S., Baldwin, A. G., Freeman, S., et al. (2016). Fenamate NSAIDs inhibit the NLRP3 inflammasome and protect against Alzheimer's disease in rodent models. Nature communications 7, 12504.

de Alba, E. (2009). Structure and interdomain dynamics of apoptosis-associated speck-like protein containing a CARD (ASC). J Biol Chem 284, 32932-32941.

de Almeida, L., Khare, S., Misharin, A. V., Patel, R., Ratsimandresy, R. A., Wallin, M. C., Perlman, H., Greaves, D. R., Hoffman, H. M., Dorfleutner, A., et al. (2015). The PYRIN domain-only protein POP1 inhibits inflammasome assembly and ameliorates inflammatory disease. Immunity 43, 264-276.

Dick, M. S., Sborgi, L., Rühl, S., Hiller, S., and Broz, P. (2016). ASC filament formation serves as a signal amplification mechanism for inflammasomes. Nature communications 7, 11929.

Dorfleutner, A., Bryan, N. B., Talbott, S. J., Funya, K. N., Rellick, S. L., Reed, J. C., Shi, X., Rojanasakul, Y., Flynn, D. C., and Stehlik, C. (2007a). Cellular pyrin domain-only protein 2 is a candidate regulator of inflammasome activation. Infect Immun 75, 1484-1492.

Dorfleutner, A., Talbott, S. J., Bryan, N. B., Funya, K. N., Rellick, S. L., Reed, J. C., Shi, X., Rojanasakul, Y., Flynn, D. C., and Stehlik, C. (2007b). A Shope Fibroma virus PYRIN-only protein modulates the host immune response. Virus Genes 35, 685-694.

Dougherty, D. A. (1996). Cation-π interactions in chemistry and biology: a new view of benzene, Phe, Tyr, and Trp. Science 271, 163-168.

Dougherty, D. A. (2013). The cation-π interaction. Accounts of chemical research 46, 885-893.

Doyle, S. L., Campbell, M., Ozaki, E., Salomon, R. G., Mori, A., Kenna, P. F., Farrar, G. J., *Kiang*, A.-S., Humphries, M. M., Lavelle, E. C., et al. (2012). NLRP3 has a protective role in age-related macular degeneration through the induction of IL-18 by drusen components. Nat Med 18, 791-798.

Ehrchen, J. M., Sunderkötter, C., Foell, D., Vogl, T., and Roth, J. (2009). The endogenous Toll-like receptor 4 agonist S100A8/S100A9 (calprotectin) as innate amplifier of infection, autoimmunity, and cancer. J Leukoc Biol 86, 557-566.

Epling-Burnette, P. K., McDaniel, J., Wei, S., and List, A. F. (2012). Emerging immunosuppressive drugs in myelodysplastic syndromes. Expert Opin Emerg Drugs 17, 519-541.

Fang, J., Barker, B., Bolanos, L., Liu, X., Jerez, A., Makishima, H., Christie, S., Chen, X., Rao, D. S., Grimes, H. L., et al. (2014). Myeloid malignancies with chromosome 5q deletions acquire a dependency on an intrachromosomal NF-κB gene network. Cell Rep 8, 1328-1338.

Fang, J., Rhyasen, G., Bolanos, L., Rasch, C., Varney, M., Wunderlich, M., Goyama, S., Jansen, G., Cloos, J., Rigolino, C., et al. (2012). Cytotoxic effects of bortezomib in myelodysplastic syndrome/acute myeloid leukemia depend on autophagy-mediated lysosomal degradation of TRAF6 and repression of PSMA1. Blood 120, 858-867.

Farquhar, M. J., and Bowen, D. T. (2003). Oxidative stress and the myelodysplastic syndromes. Int J Hematol 77, 342-350.

Fernandes-Alnemri, T., Wu, J., Yu, J.-W., Datta, P., Miller, B., Jankowski, W., Rosenberg, S., Zhang, J., and Alnemri, E. S. (2007). The pyroptosome: a supramolecular assembly of ASC dimers mediating inflammatory cell death via caspase-1 activation. Cell death and differentiation 14, 1590-1604.

Fowler, B. J., Gelfand, B. D., Kim, Y., Kerur, N., Tarallo, V., Hirano, Y., Amarnath, S., Fowler, D. H., Radwan, M., Young, M. T., et al. (2014). Nucleoside reverse transcriptase inhibitors possess intrinsic anti-inflammatory activity. Science 346, 1000-1003.

Franklin, B. S., Bossaller, L., De Nardo, D., Ratter, J. M., Stutz, A., Engels, G., Brenker, C., Nordhoff, M., Mirandola, S. R., Al-Amoudi, A., et al. (2014). The adaptor ASC has extracellular and 'prionoid' activities that propagate inflammation. Nat Immunol 15, 727-737.

Fulp, J., He, L., Toldo, S., Jiang, Y., Boice, A., Guo, C., Li, X., Rolfe, A., Sun, D., Abbate, A., et al. (2018). Structural Insights of Benzenesulfonamide Analogues as NLRP3 Inflammasome Inhibitors: Design, Synthesis, and Biological Characterization. Journal of medicinal chemistry 61, 5412-5423.

Gangat, N., Patnaik, M. M., and Tefferi, A. (2016). Myelodysplastic syndromes: contemporary review and how we treat. Am J Hematol 91, 76-89.

Greenfield, N. J. (2006). Using circular dichroism spectra to estimate protein secondary structure. Nature protocols 1, 2876-2890.

Haferlach, T., Nagata, Y., Grossmann, V., Okuno, Y., Bacher, U., Nagae, G., Schnittger, S., Sanada, M., Kon, A., Alpermann, T., et al. (2014). Landscape of genetic lesions in 944 patients with myelodysplastic syndromes. Leukemia 28, 241-247.

Harijith, A., Ebenezer, D. L., and Natarajan, V. (2014). Reactive oxygen species at the crossroads of inflammasome and inflammation. Front Physiol 5, 352.

Hill, J. R., Coll, R. C., Sue, N., Reid, J. C., Dou, J., Holley, C. L., Pelingon, R., Dickinson, J. B., Biden, T. J., Schroder, K., et al. (2017). Sulfonylureas as Concomitant Insulin Secretagogues and NLRP3 Inflammasome Inhibitors. Chem Med Chem 12, 1449-1457.

Hofmann, W.-K., de Vos, S., Komor, M., Hoelzer, D., Wachsman, W., and Koeffler, H. P. (2002). Characterization of gene expression of $CD34^+$ cells from normal and myelodysplastic bone marrow. Blood 100, 3553-3560.

Hoss, F., Rodriguez-Alcazar, J. F., and Latz, E. (2017). Assembly and regulation of ASC specks. Cellular and molecular life sciences: CMLS 74, 1211-1229.

Jiang, H., He, H., Chen, Y., Huang, W., Cheng, J., Ye, J., Wang, A., Tao, J., Wang, C., Liu, Q., et al. (2017). Identification of a selective and direct NLRP3 inhibitor to treat inflammatory disorders. J Exp Med 214, 3219-3238.

Johnston, J. B., Barrett, J. W., Nazarian, S. H., Goodwin, M., Ricciuto, D., Wang, G., and McFadden, G. (2005). A poxvirus-encoded pyrin domain protein interacts with ASC-1 to inhibit host inflammatory and apoptotic responses to infection. Immunity 23, 587-598.

Kajla, S., Mondol, A. S., Nagasawa, A., Zhang, Y., Kato, M., Matsuno, K., Yabe-Nishimura, C., and Kamata, T. (2012). A crucial role for Nox 1 in redox-dependent regulation of Wnt-β-catenin signaling. FASEB J 26, 2049-2059.

Khare, S., Ratsimandresy, R. A., de Almeida, L., Cuda, C. M., Rellick, S. L., Misharin, A. V., Wallin, M. C., Gangopadhyay, A., Forte, E., Gottwein, E., et al. (2014). The PYRIN domain-only protein POP3 inhibits ALR inflammasomes and regulates responses to infection with DNA viruses. Nat Immunol 15, 343-353.

Klepin, H. D., Rao, A. V., and Pardee, T. S. (2014). Acute myeloid leukemia and myelodysplastic syndromes in older adults. Journal of clinical oncology: official journal of the American Society of Clinical Oncology 32, 2541-2552.

Koike, M., Ishiyama, T., Tomoyasu, S., and Tsuruoka, N. (1995). Spontaneous cytokine overproduction by peripheral blood mononuclear cells from patients with myelodysplastic syndromes and aplastic anemia. Leuk Res 19, 639-644.

Laliberte, R. E., Perregaux, D. G., Hoth, L. R., Rosner, P. J., Jordan, C. K., Peese, K. M., Eggler, J. F., Dombroski, M. A., Geoghegan, K. F., and Gabel, C. A. (2003). Glutathione s-transferase omega 1-1 is a target of cytokine release inhibitory drugs and may be responsible for their effect on interleukin-1β posttranslational processing. J Biol Chem 278, 16567-16578.

Lamkanfi, M., and Dixit, V. M. (2012). Inflammasomes and their roles in health and disease. Annu Rev Cell Dev Biol 28, 137-161.

Lamkanfi, M., and Dixit, V. M. (2014). Mechanisms and functions of inflammasomes. Cell 157, 1013-1022.

Lamkanfi, M., Mueller, J. L., Vitari, A. C., Misaghi, S., Fedorova, A., Deshayes, K., Lee, W. P., Hoffman, H. M., and Dixit, V. M. (2009). Glyburide inhibits the Cryopyrin/Nalp3 inflammasome. J Cell Biol 187, 61-70.

Latz, E., Xiao, T. S., and Stutz, A. (2013). Activation and regulation of the inflammasomes. Nat Rev Immunol 13, 397-411.

Liepinsh, E., Barbals, R., Dahl, E., Sharipo, A., Staub, E., and Otting, G. (2003). The death-domain fold of the ASC PYRIN domain, presenting a basis for PYRIN/PYRIN recognition. J Mol Biol 332, 1155-1163.

Lindsley, R. C., Saber, W., Mar, B. G., Redd, R., Wang, T., Haagenson, M. D., Grauman, P. V., Hu, Z.-H., Spellman, S. R., Lee, S. J., et al. (2017). Prognostic mutations in myelodysplastic syndrome after stem-cell transplantation. The New England journal of medicine 376, 536-547.

Lönn, P., and Dowdy, S. F. (2015). Cationic PTD/CPP-mediated macromolecular delivery: charging into the cell. Expert opinion on drug delivery 12, 1627-1636.

Lu, A., Magupalli, V. G., Ruan, J., Yin, Q., Atianand, M. K., Vos, M. R., Schröder, G. F., Fitzgerald, K. A., Wu, H., and Egelman, E. H. (2014). Unified polymerization mechanism for the assembly of ASC-dependent inflammasomes. Cell 156, 1193-1206.

Man, S. M., and Kanneganti, T.-D. (2016). Converging roles of caspases in inflammasome activation, cell death and innate immunity. Nat Rev Immunol 16, 7-21.

Maratheftis, C. I., Andreakos, E., Moutsopoulos, H. M., and Voulgarelis, M. (2007). Toll-like receptor-4 is up-regulated in hematopoietic progenitor cells and contributes to increased apoptosis in myelodysplastic syndromes. Clin Cancer Res 13, 1154-1160.

Marchetti, C., Chojnacki, J., Toldo, S., Mezzaroma, E., Tranchida, N., Rose, S. W., Federici, M., Van Tassell, B. W., Zhang, S., and Abbate, A. (2014). A novel pharmacologic inhibitor of the NLRP3 inflammasome limits myocardial injury after ischemia-reperfusion in the mouse. J Cardiovasc Pharmacol 63, 316-322.

Masters, S. L., Dunne, A., Subramanian, S. L., Hull, R. L., Tannahill, G. M., Sharp, F. A., Becker, C., Franchi, L., Yoshihara, E., Chen, Z., et al. (2010). Activation of the NLRP3 inflammasome by islet amyloid polypeptide provides a mechanism for enhanced IL-1β in type 2 diabetes. Nat Immunol 11, 897-904.

Mundle, S. D., Venugopal, P., Cartlidge, J. D., Pandav, D. V., Broady-Robinson, L., Gezer, S., Robin, E. L., Rifkin, S. R., Klein, M., Alston, D. E., et al. (1996). Indication of an involvement of interleukin-1β converting enzyme-like protease in intramedullary apoptotic cell death in the bone marrow of patients with myelodysplastic syndromes. Blood 88, 2640-2647.

Muñoz-Planillo, R., Kuffa, P., Martínez-Colón, G., Smith, B. L., Rajendiran, T. M., and Núñez, G. (2013). K$^+$ efflux is the common trigger of NLRP3 inflammasome activation by bacterial toxins and particulate matter. Immunity 38, 1142-1153.

Natarajan, A., Ghose, R., and Hill, J. M. (2006). Structure and dynamics of ASC2, a pyrin domain-only protein that regulates inflammatory signaling. J Biol Chem 281, 31863-31875.

O'Brien, M., Moehring, D., Muñoz-Planillo, R., Núñez, G., Callaway, J., Ting, J., Scurria, M., Ugo, T., Bernad, L., Cali, J., et al. (2017). A bioluminescent caspase-1 activity assay rapidly monitors inflammasome activation in cells. Journal of immunological methods 447, 1-13.

Oroz, J., Barrera-Vilarmau, S., Alfonso, C., Rivas, G., and de Alba, E. (2016). ASC pyrin domain self-associates and binds NLRP3 protein using equivalent binding interfaces. J Biol Chem 291, 19487-19501.

Ortmann, C. A., Kent, D. G., Nangalia, J., Silber, Y., Wedge, D. C., Grinfeld, J., Baxter, E. J., Massie, C. E., Papaemmanuil, E., Menon, S., et al. (2015). Effect of mutation order on myeloproliferative neoplasms. The New England journal of medicine 372, 601-612.

Papaemmanuil, E., Gerstung, M., Malcovati, L., Tauro, S., Gundem, G., Van Loo, P., Yoon, C. J., Ellis, P., Wedge, D. C., Pellagatti, A., et al. (2013). Clinical and biological implications of driver mutations in myelodysplastic syndromes. Blood 122, 3616-3627; quiz 3699.

Perregaux, D. G., McNiff, P., Laliberte, R., Hawryluk, N., Peurano, H., Stam, E., Eggler, J., Griffiths, R., Dombroski, M. A., and Gabel, C. A. (2001). Identification and characterization of a novel class of interleukin-1 post-translational processing inhibitors. J Pharmacol Exp Ther 299, 187-197.

Porter, K. A., Duffy, E. B., Nyland, P., Atianand, M. K., Sharifi, H., and Harton, J. A. (2014). The CLRX.1/NOD24 (NLRP2P) pseudogene codes a functional negative regulator of NF-kappaB, pyrin-only protein 4. Genes and immunity 15, 392-403.

Pyatt, D. W., Stillman, W. S., Yang, Y., Gross, S., Zheng, J. H., and Irons, R. D. (1999). An essential role for NF-κB in human CD34$^+$ bone marrow cell survival. Blood 93, 3302-3308.

Rassool, F. V., Gaymes, T. J., Omidvar, N., Brady, N., Beurlet, S., Pla, M., Reboul, M., Lea, N., Chomienne, C., Thomas, N. S. B., et al. (2007). Reactive oxygen species, DNA damage, and error-prone repair: a model for genomic instability with progression in myeloid leukemia? Cancer Res 67, 8762-8771.

Rathinam, V. A., and Fitzgerald, K. A. (2016). Inflammasome complexes: emerging mechanisms and effector functions. Cell 165, 792-800.

Rathinam, V. A., Vanaja, S. K., and Fitzgerald, K. A. (2012). Regulation of inflammasome signaling. Nat Immunol 13, 333-342.

Reboldi, A., Dang, E. V., McDonald, J. G., Liang, G., Russell, D. W., and Cyster, J. G. (2014). Inflammation. 25-Hydroxycholesterol suppresses interleukin-1-driven inflammation downstream of type I interferon. Science 345, 679-684.

Rharass, T., Lemcke, H., Lantow, M., Kuznetsov, S. A., Weiss, D. G., and Panakova, D. (2014). Ca$^{2+}$-mediated mitochondrial reactive oxygen species metabolism augments Wnt/β-catenin pathway activation to facilitate cell differentiation. J Biol Chem 289, 27937-27951.

Rhyasen, G. W., Bolanos, L., Fang, J., Jerez, A., Wunderlich, M., Rigolino, C., Mathews, L., Ferrer, M., Southall, N., Guha, R., et al. (2013). Targeting IRAK1 as a therapeutic approach for myelodysplastic syndrome. Cancer Cell 24, 90-104.

Sallmyr, A., Fan, J., and Rassool, F. V. (2008). Genomic instability in myeloid malignancies: increased reactive oxygen species (ROS), DNA double strand breaks (DSBs) and error-prone repair. Cancer Lett 270, 1-9.

Sawanobori, M., Yamaguchi, S., Hasegawa, M., Inoue, M., Suzuki, K., Kamiyama, R., Hirokawa, K., and Kitagawa, M. (2003). Expression of TNF receptors and related signaling molecules in the bone marrow from patients with myelodysplastic syndromes. Leuk Res 27, 583-591.

Sborgi, L., Ravotti, F., Dandey, V. P., Dick, M. S., Mazur, A., Reckel, S., Chami, M., Scherer, S., Huber, M., Böckmann, A., et al. (2015). Structure and assembly of the mouse ASC inflammasome by combined NMR spectroscopy and cryo-electron microscopy. Proc Natl Acad Sci USA 112, 13237-13242.

Schneider, R. K., Schenone, M., Ferreira, M. V., Kramann, R., Joyce, C. E., Hartigan, C., Beier, F., Brummendorf, T.

H., Germing, U., Platzbecker, U., et al. (2016). Rps14 haploinsufficiency causes a block in erythroid differentiation mediated by S100A8 and S100A9. Nat Med 22, 288-297.

Schroder, K., and Tschopp, J. (2010). The inflammasomes. Cell 140, 821-832.

Sharma, D., and Kanneganti, T.-D. (2016). The cell biology of inflammasomes: mechanisms of inflammasome activation and regulation. J Cell Biol 213, 617-629.

Shetty, V., Mundle, S., Alvi, S., Showel, M., Broady-Robinson, L., Dar, S., Borok, R., Showel, J., Gregory, S., Rifkin, S., et al. (1996). Measurement of apoptosis, proliferation and three cytokines in 46 patients with myelodysplastic syndromes. Leuk Res 20, 891-900.

Simard, J.-C., Cesaro, A., Chapeton-Montes, J., Tardif, M., Antoine, F., Girard, D., and Tessier, P. A. (2013). S100A8 and S100A9 induce cytokine expression and regulate the NLRP3 inflammasome via ROS-dependent activation of NF-κB$^1$. PLOS One 8, e72138.

Starczynowski, D. T., Kuchenbauer, F., Argiropoulos, B., Sung, S., Morin, R., Muranyi, A., Hirst, M., Hogge, D., Marra, M., Wells, R. A., et al. (2010). Identification of miR-145 and miR-146a as mediators of the 5q-syndrome phenotype. Nat Med 16, 49-58.

Stehlik, C., Krajewska, M., Welsh, K., Krajewski, S., Godzik, A., and Reed, J. C. (2003). The PAAD/PYRIN-only protein POP1/ASC2 is a modulator of ASC-mediated nuclear-factor-KB and pro-caspase-1 regulation. Biochem J 373, 101-113.

Stutz, A., Horvath, G. L., Monks, B. G., and Latz, E. (2013). ASC speck formation as a readout for inflammasome activation. Methods in molecular biology (Clifton, NJ) 1040, 91-101.

Tang, T., Lang, X., Xu, C., Wang, X., Gong, T., Yang, Y., Cui, J., Bai, L., Wang, J., Jiang, W., et al. (2017). CLICs-dependent chloride efflux is an essential and proximal upstream event for NLRP3 inflammasome activation. Nature communications 8, 202.

Tefferi, A., and Vardiman, J. W. (2009). Myelodysplastic syndromes. The New England journal of medicine 361, 1872-1885.

Vajjhala, P. R., Mirams, R. E., and Hill, J. M. (2012). Multiple binding sites on the pyrin domain of ASC protein allow self-association and interaction with NLRP3 protein. J Biol Chem 287, 41732-41743.

Vanaja, S. K., Rathinam, V. A. K., and Fitzgerald, K. A. (2015). Mechanisms of inflammasome activation: recent advances and novel insights. Trends Cell Biol 25, 308-315.

Velegraki, M., Papakonstanti, E., Mavroudi, I., Psyllaki, M., Tsatsanis, C., Oulas, A., Iliopoulos, I., Katonis, P., and Papadaki, H. A. (2013). Impaired clearance of apoptotic cells leads to HMGB1 release in the bone marrow of patients with myelodysplastic syndromes and induces TLR4-mediated cytokine production. Haematologica 98, 1206-1215.

Vogl, T., Tenbrock, K., Ludwig, S., Leukert, N., Ehrhardt, C., van Zoelen, M. A. D., Nacken, W., Foell, D., van der Poll, T., Sorg, C., et al. (2007). Mrp8 and Mrp14 are endogenous activators of Toll-like receptor 4, promoting lethal, endotoxin-induced shock. Nat Med 13, 1042-1049.

Wei, Y., Chen, R., Dimicoli, S., Bueso-Ramos, C., Neuberg, D., Pierce, S., Wang, H., Yang, H., Jia, Y., Zheng, H., et al. (2013a). Global H3K4me3 genome mapping reveals alterations of innate immunity signaling and overexpression of JMJD3 in human myelodysplastic syndrome CD34+ cells. Leukemia 27, 2177-2186.

Wei, Y., Dimicoli, S., Bueso-Ramos, C., Chen, R., Yang, H., Neuberg, D., Pierce, S., Jia, Y., Zheng, H., Wang, H., et al. (2013b). Toll-like receptor alterations in myelodysplastic syndrome. Leukemia 27, 1832-1840.

Welch, J. S., Petti, A. A., Miller, C. A., Fronick, C. C., O'Laughlin, M., Fulton, R. S., Wilson, R. K., Baty, J. D., Duncavage, E. J., Tandon, B., et al. (2016). TP53 and decitabine in acute myeloid leukemia and myelodysplastic syndromes. The New England journal of medicine 375, 2023-2036.

Wetzler, M., Kurzrock, R., Estrov, Z., Estey, E., and Talpaz, M. (1995). Cytokine expression in adherent layers from patients with myelodysplastic syndrome and acute myelogenous leukemia. Leuk Res 19, 23-34.

Yoshida, K., Sanada, M., Shiraishi, Y., Nowak, D., Nagata, Y., Yamamoto, R., Sato, Y., Sato-Otsubo, A., Kon, A., Nagasaki, M., et al. (2011). Frequent pathway mutations of splicing machinery in myelodysplasia. Nature 478, 64-69.

Yoshizato, T., Dumitriu, B., Hosokawa, K., Makishima, H., Yoshida, K., Townsley, D., Sato-Otsubo, A., Sato, Y., Liu, D., Suzuki, H., et al. (2015). Somatic mutations and clonal hematopoiesis in aplastic anemia. The New England journal of medicine 373, 35-47.

Youm, Y.-H., Nguyen, K. Y., Grant, R. W., Goldberg, E. L., Bodogai, M., Kim, D., D'Agostino, D., Planavsky, N., Lupfer, C., Kanneganti, T. D., et al. (2015). The ketone metabolite β-hydroxybutyrate blocks NLRP3 inflammasome-mediated inflammatory disease. Nat Med 21, 263-269.

Zhao, J. L., Rao, D. S., Boldin, M. P., Taganov, K. D., O'Connell, R. M., and Baltimore, D. (2011). NF-κB dysregulation in microRNA-146a-deficient mice drives the development of myeloid malignancies. Proc Natl Acad Sci USA 108, 9184-9189.

Zhao, J. L., Rao, D. S., O'Connell, R. M., Garcia-Flores, Y., and Baltimore, D. (2013).

MicroRNA-146a acts as a guardian of the quality and longevity of hematopoietic stem cells in mice. Elife 2, e00537.

Zhou, R., Tardivel, A., Thorens, B., Choi, I., and Tschopp, J. (2010). Thioredoxin-interacting protein links oxidative stress to inflammasome activation. Nat Immunol 11, 136-140.

What is claimed is:

1. A peptide comprising a H2 helix of a pyrin domain; wherein the peptide consists of only one pyrin domain helical structure; wherein the peptide is 15 amino acids or less; and wherein at least two non-consecutive amino acids of the H2 helix are covalently linked.

2. The peptide of claim 1, wherein the peptide comprises fSAH-POP1-1 (SEQ ID NO: 1), fSAH-POP1-3 (SEQ ID NO: 3), fSAH-POP1-4 (SEQ ID NO: 4), fSAH-POP1-5 (SEQ ID NO: 5), fSAH-POP1-6 (SEQ ID NO: 6), fSAH-POP1-7 (SEQ ID NO: 7), fSAH-POP1-8 (SEQ ID NO: 8), fSAH-POP1-9 (SEQ ID NO: 9), fSAH-POP1-10 (SEQ ID NO: 10), fSAH-POP1-11 (SEQ ID NO: 11), fSAH-POP1-12 (SEQ ID NO: 12), fSAH-POP1-13 (SEQ ID NO: 13), fSAH-POP1-14 (SEQ ID NO: 14), fSAH-POP1-15 (SEQ ID NO: 15), fSAH-POP1-16 (SEQ ID NO: 16), fSAH-POP1-17 (SEQ ID NO: 17), fSAH-POP1-18 (SEQ ID NO: 18), fSAH-POP1-19 (SEQ ID NO: 19), fSAH-POP1-20 (SEQ ID NO: 20), fSAH-POP1-21 (SEQ ID NO: 21), fSAH-POP1-22 (SEQ ID NO: 22), fSAH-POP1-23 (SEQ ID NO: 23), fSAH-POP1-24 (SEQ ID NO: 24), fSAH-POP1-25 (SEQ ID NO: 25), fSAH-POP1-26 (SEQ ID NO: 26), fSAH-POP1-27 (SEQ ID NO: 27), fSAH-POP1-28 (SEQ ID NO: 28), fSAH-POP1-29 (SEQ ID NO: 29), fSAH-POP1-30 (SEQ ID NO: 30), fSAH-POP1-31 (SEQ ID NO: 31), SAH-POP1-1 (SEQ ID NO: 32), SAH-POP1-2 (SEQ ID NO: 33), SAH-POP1-3 (SEQ ID NO: 34), SAH-POP1-4 (SEQ ID NO: 35), SAH-POP1-5 (SEQ ID NO: 36), SAH-POP1-6 (SEQ ID NO: 37), SAH-POP1-7 (SEQ ID NO: 38), SAH-POP1-8 (SEQ ID NO: 39), SAH-POP1-17 (SEQ ID NO: 44), and/or SAH-POP1-18 (SEQ ID NO: 45).

* * * * *

SEQUENCE LISTING

<160> NUMBER OF SEQ ID NOS: 45

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

```
<220> FEATURE:
<221> NAME/KEY: MISC_FEATURE
<222> LOCATION: (1)..(1)
<223> OTHER INFORMATION: X = B=betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (8)..(8)
<223> OTHER INFORMATION: X =NL = norleucine

<400> SEQUENCE: 1

Xaa Glu Xaa Lys Lys Phe Xaa Xaa Lys Leu Gly Thr Val
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (9)..(9)
<223> OTHER INFORMATION: X = NL = norleucine

<400> SEQUENCE: 2

Xaa Glu Glu Leu Lys Lys Phe Lys Xaa Lys Leu Gly Thr Val
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (8)..(8)
<223> OTHER INFORMATION: X = NL = norleucine
<220> FEATURE:
<221> NAME/KEY: MISC_FEATURE
<222> LOCATION: (10)..(10)
<223> OTHER INFORMATION: X= S5=(S)-2-(4-pentenyl)alanineS5, the two Xs
      are also directly connected by a double bond

<400> SEQUENCE: 3

Xaa Glu Leu Lys Lys Xaa Lys Xaa Lys Xaa Gly Thr Val
1               5                   10

<210> SEQ ID NO 4
<211> LENGTH: 14
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= NL = norleucine

<400> SEQUENCE: 4

Xaa Glu Xaa Leu Lys Lys Xaa Lys Xaa Lys Leu Gly Thr Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= NL = norleucine

<400> SEQUENCE: 5

Xaa Gln Xaa Leu Lys Lys Xaa Lys Xaa Lys Leu Gly Thr Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X = S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X = S5=(S)-2-(4-pentenyl)alanineS5, the two Xs
```

```
  are also directly connected by a double bond
<220> FEATURE:
<221> NAME/KEY: MISC_FEATURE
<222> LOCATION: (9)..(9)
<223> OTHER INFORMATION: X = NL = norleucine

<400> SEQUENCE: 6

Xaa Gln Xaa Leu Lys Lys Xaa Lys Xaa Lys Leu Trp Thr Ala
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X = S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X = S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X = NL = norleucine

<400> SEQUENCE: 7

Xaa Gln Xaa Leu Lys Lys Xaa Lys Xaa Lys Leu Gln Thr Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= NL = norleucine

<400> SEQUENCE: 8

Xaa Gln Xaa Leu Lys Lys Xaa Lys Xaa Lys Gln Trp Thr Ala
1               5                   10

<210> SEQ ID NO 9
<211> LENGTH: 14
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X = S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X = S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X = NL = norleucine

<400> SEQUENCE: 9

Xaa Gln Xaa Leu Lys Lys Xaa Gln Xaa Lys Leu Trp Thr Ala
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= NL = norleucine

<400> SEQUENCE: 10

Xaa Gln Xaa Leu Arg Lys Xaa Gln Xaa Lys Leu Trp Thr Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 11
```

```
Xaa Gln Xaa Leu Arg Lys Xaa Gln Phe Lys Leu Trp Thr Ala
1               5                   10
```

<210> SEQ ID NO 12
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 12

```
Xaa Gln Xaa Leu Arg Lys Xaa Gln Trp Lys Leu Trp Thr Ala
1               5                   10
```

<210> SEQ ID NO 13
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 13

```
Xaa Gln Xaa Leu Arg Arg Xaa Gln Trp Lys Leu Trp Thr Ala
1               5                   10
```

<210> SEQ ID NO 14
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 14

Xaa Gln Xaa Leu Arg Arg Xaa Gln Trp Lys Leu Trp Asn Ala
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 15

Xaa Gln Xaa Leu Arg Arg Xaa Gln Trp Lys Leu Trp Gln Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 16

Xaa Gln Xaa Leu Arg Arg Xaa Gln Trp Lys Leu Trp Thr Ser
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)

```
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 17

Xaa Gln Xaa Leu Arg Arg Xaa Gln Trp Xaa Leu Trp Thr Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond

<400> SEQUENCE: 18

Xaa Gln Xaa Leu Arg Arg Xaa Gln Trp Phe Leu Trp Thr Ala
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X = (1-Nal)

<400> SEQUENCE: 19

Xaa Gln Xaa Leu Arg Arg Xaa Gln Xaa Lys Leu Trp Thr Ala
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X = (2-Nal)

<400> SEQUENCE: 20

Xaa Gln Xaa Leu Arg Arg Xaa Gln Xaa Lys Leu Trp Thr Ala
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X = (1-Nal)
<220> FEATURE:
<221> NAME/KEY: MISC_FEATURE
<222> LOCATION: (10)..(10)
<223> OTHER INFORMATION: X = NL = norleucine

<400> SEQUENCE: 21

Xaa Gln Xaa Leu Arg Arg Xaa Gln Xaa Xaa Leu Trp Thr Ala
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
```

```
<221> NAME/KEY: MISC_FEATURE
<222> LOCATION: (9)..(9)
<223> OTHER INFORMATION: X= (2-Nal)
<220> FEATURE:
<221> NAME/KEY: MISC_FEATURE
<222> LOCATION: (10)..(10)
<223> OTHER INFORMATION: X= NL = norleucine

<400> SEQUENCE: 22

Xaa Gln Xaa Leu Arg Arg Xaa Gln Xaa Leu Trp Thr Ala
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 23

Xaa Gln Xaa Leu Arg Arg Xaa Gln Trp Xaa Arg Trp Thr Ala
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 24

Xaa Gln Xaa Ser Arg Arg Xaa Gln Trp Xaa Arg Trp Thr Ala
1               5                   10

<210> SEQ ID NO 25
<211> LENGTH: 14
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 25

Xaa Gln Xaa Leu Arg Arg Xaa Gln Trp Xaa Gln Trp Thr Ala
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 26

Xaa Gln Xaa Ser Arg Arg Xaa Gln Trp Xaa Gln Trp Thr Ala
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
```

```
<220> FEATURE:
<221> NAME/KEY: MISC_FEATURE
<222> LOCATION: (10)..(10)
<223> OTHER INFORMATION: X= NL = norleucine

<400> SEQUENCE: 27

Xaa Gln Xaa Ser Arg Arg Xaa Lys Trp Xaa Gln Trp Thr Ala
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 28

Xaa Gln Xaa Leu Arg Arg Xaa Gln Trp Xaa Leu Gly Thr Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 29

Xaa Gln Xaa Leu Arg Arg Xaa Gln Trp Xaa Leu Asp Thr Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic construct
```

-continued

```
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 30

Xaa Gln Xaa Leu Arg Arg Xaa Gln Trp Xaa Leu Asn Thr Ala
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: X = betaA = beta-alanine
<220> FEATURE:
<221> NAME/KEY: MISC_FEATURE
<222> LOCATION: (3)..(3)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (7)..(7)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (10)..(10)
<223> OTHER INFORMATION: X= NL = norleucine

<400> SEQUENCE: 31

Xaa Gln Xaa Leu Arg Arg Xaa Gln Trp Xaa Leu Ser Thr Ala
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
      are also directly connected by a double bond

<400> SEQUENCE: 32

Glu Xaa Lys Lys Phe Xaa Met Lys Leu Gly Thr Val
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = R8 = Fmoc-(R)-2-(7-octenyl)alanine-OH, an O
      and an X are also directly connected by a double bond
<220> FEATURE:
<221> NAME/KEY: MISC_FEATURE
<222> LOCATION: (9)..(9)
<223> OTHER INFORMATION: X= S5=(S)-2-(4-pentenyl)alanineS5, the two Xs
      are also directly connected by a double bond

<400> SEQUENCE: 33

Glu Xaa Lys Lys Phe Lys Met Lys Xaa Gly Thr Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= S5=(S)-2-(4-pentenyl)alanineS5, the two Xs
      are also directly connected by a double bond

<400> SEQUENCE: 34

Glu Leu Lys Lys Xaa Lys Met Lys Xaa Gly Thr Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
      are also directly connected by a double bond

<400> SEQUENCE: 35

Glu Xaa Leu Lys Lys Xaa Lys Met Lys Leu Gly Thr Val
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
``` are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
        are also directly connected by a double bond

<400> SEQUENCE: 36

Glu Xaa Leu Lys Lys Xaa Lys Trp Lys Leu Gly Thr Ala
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic construct

<400> SEQUENCE: 37

Glu Ser Leu Lys Lys Ser Lys Phe Lys Leu Gly Thr Ala
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
        are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
        are also directly connected by a double bond

<400> SEQUENCE: 38

Glu Xaa Leu Lys Lys Xaa Lys His Lys Leu Gly Thr Ala
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
        are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
        are also directly connected by a double bond

<400> SEQUENCE: 39

Glu Xaa Leu Lys Lys Xaa Lys Glx Lys Leu Gly Thr Ala
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 40

Glu Glu Leu Lys Lys Phe Lys Met Lys Leu Gly Thr Val
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Synthetic construct

<400> SEQUENCE: 41

Leu Thr Ala Glu Glu Leu Lys Lys Phe Lys Leu Lys Leu Leu Ser Val
1               5                   10                  15

Pro Leu Arg Glu Gly
            20

<210> SEQ ID NO 42
<211> LENGTH: 21
<212> TYPE: PRT
<213> ORGANISM: Artificial Sequence
<220> FEATURE:
<223> OTHER INFORMATION: Synthetic construct

<400> SEQUENCE: 42

Leu Glu Asp Val Asp Leu Lys Lys Phe Lys Met His Leu Glu Asp Tyr
1               5                   10                  15

Pro Pro Gln Lys Gly
            20

<210> SEQ ID NO 43
<211> LENGTH: 21
<212> TYPE: PRT
<213> ORGANISM: Artificial Sequence
<220> FEATURE:
<223> OTHER INFORMATION: Synthetic construct

<400> SEQUENCE: 43

Leu Thr Pro Glu Glu Leu Lys Lys Phe Lys Met Lys Leu Gly Thr Val
1               5                   10                  15

Pro Leu Arg Glu Gly
            20

<210> SEQ ID NO 44
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (9)..(9)
<223> OTHER INFORMATION: X= NL = norleucine

<400> SEQUENCE: 44

Gln Xaa Leu Arg Arg Xaa Gln Trp Xaa Leu Trp Thr Ala
1               5                   10
```

```
<210> SEQ ID NO 45
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= S5=(S)-2-(4-pentenyl)alanineS5, the two Xs
      are also directly connected by a double bond
<220> FEATURE:
<221> NAME/KEY: MISC_FEATURE
<222> LOCATION: (6)..(6)
<223> OTHER INFORMATION: X= S5=(S)-2-(4-pentenyl)alanineS5, the two Xs
      are also directly connected by a double bond

<400> SEQUENCE: 45

Gln Xaa Leu Arg Arg Xaa Gln Trp Phe Leu Trp Thr Ala
1               5                   10
```